(12) United States Patent
James et al.

(10) Patent No.: US 9,291,557 B2
(45) Date of Patent: Mar. 22, 2016

(54) LOCALIZED SURFACE PLASMON RESONANCE MERCURY DETECTION SYSTEM AND METHODS

(71) Applicant: The Regents of the University of California, Oakland, CA (US)

(72) Inventors: Jay James, Berkeley, CA (US); Donald Lucas, Moraga, CA (US); Jeffrey Scott Crosby, Berkeley, CA (US); Catherine P. Koshland, Atherton, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/368,499

(22) PCT Filed: Jan. 10, 2013

(86) PCT No.: PCT/US2013/021066
§ 371 (c)(1),
(2) Date: Jun. 24, 2014

(87) PCT Pub. No.: WO2013/106598
PCT Pub. Date: Jul. 18, 2013

(65) Prior Publication Data
US 2014/0333933 A1 Nov. 13, 2014

Related U.S. Application Data

(60) Provisional application No. 61/585,542, filed on Jan. 11, 2012, provisional application No. 61/587,546, filed on Jan. 17, 2012.

(51) Int. Cl.
*G01N 21/55* (2014.01)
*G01N 21/552* (2014.01)
(Continued)

(52) U.S. Cl.
CPC ............... *G01N 21/554* (2013.01); *G01J 3/42* (2013.01); *G01N 33/0045* (2013.01); *G01J 2003/425* (2013.01); *G01N 2201/088* (2013.01)

(58) Field of Classification Search
CPC ... G01N 21/553; G01N 21/55; G01N 21/554; G01N 21/474; G01N 21/57
USPC .......................................................... 356/445
See application file for complete search history.

(56) References Cited

U.S. PATENT DOCUMENTS 7,314,507 B1 * 1/2008 Ganesan .......................... 95/134
7,485,419 B2 * 2/2009 Lu ........................ C12N 15/113
435/6.1

(Continued)

FOREIGN PATENT DOCUMENTS

KR 1020110047921 5/2011

OTHER PUBLICATIONS

Chemnasiri; et al. "Gold nanorod-based mercury sensor using functionalized glass substrates", Sensors and Actuators B: Chemical (2012), 7 pages.

(Continued)

*Primary Examiner* — Tarifur Chowdhury
*Assistant Examiner* — Md Rahman
(74) *Attorney, Agent, or Firm* — Rudy J. Ng; Bret E. Field; Bozicevic, Field & Francis LLP

(57) ABSTRACT

A mercury detection system that includes a flow cell having a mercury sensor, a light source and a light detector is provided. The mercury sensor includes a transparent substrate and a submonolayer of mercury absorbing nanoparticles, e.g., gold nanoparticles, on a surface of the substrate. Methods of determining whether mercury is present in a sample using the mercury sensors are also provided. The subject mercury detection systems and methods find use in a variety of different applications, including mercury detecting applications.

20 Claims, 19 Drawing Sheets

(51) Int. Cl.
*G01N 33/00* (2006.01)
*G01J 3/42* (2006.01)

(56) References Cited

U.S. PATENT DOCUMENTS

| | | | | |
|---|---|---|---|---|
| 7,534,560 | B2* | 5/2009 | Lu | C12Q 1/34 435/287.2 |
| 2004/0218184 | A1 | 11/2004 | Jorgenson et al. | |
| 2008/0017033 | A1* | 1/2008 | Charrue et al. | 95/228 |
| 2008/0081376 | A1 | 4/2008 | Hernandez et al. | |
| 2009/0229342 | A1 | 9/2009 | Kalkan | |
| 2010/0022020 | A1 | 1/2010 | Halas et al. | |
| 2010/0128275 | A1* | 5/2010 | Chau et al. | 356/445 |
| 2010/0157426 | A1* | 6/2010 | Matsunami et al. | 359/490 |

OTHER PUBLICATIONS

Heider; et al. "Portable mercury sensor for tap water using surface plasmon resonance of immobilized gold nanorods", Talanta (2012), http://dx.doi.org/10.1016/j.talanta.2012.05.037, 6 pages.

James; et al. "Gold Nanoparticle Films As Sensitive and Reusable Elemental Mercury Sensors", Environmental Science & Technology 2012, 46, pp. 9557-9562.

Morris; et al. "A Spectroscopic Study of Mercury Vapor Adsorption on Gold Nanoparticle Films", Journal of Colloid and Interface Science 254, pp. 49-55 (2002).

Rex; et al. "Pushing the Limits of Mercury Sensors with Gold Nanorods", Anal. Chem., vol. 78, No. 2, Jan. 15, 2006, pp. 445-451.

Scallan; et al. "Optical Characterization of the Interaction of Mercury with Nanoparticulate Gold Suspended in Solution", Sensors & Transducers, vol. 85, Nov. 2007. pp. 1687-1698.

Wang, et al. (2010) "Visual detection of mercury vapor using plasmonic nanoparticle array," IEEE Sensors: 323-326.

Mirsky, et al. (2002) "Self-assembled monolayers as selective filters for chemical sensors," Nanotechnology 13(2): 175-178.

Lin et al., (2010) "Colorimetric Sensing of Silver(I) and Mercury (III) Ions Based on an Assembly of Tween 20-Stabilized Gold Nanoparticles," Anal Chem. 82(16) : 6830-3837.

* cited by examiner

LOCALIZED SURFACE PLASMON RESONANCE MERCURY DETECTION SYSTEM AND METHODS

CROSS-REFERENCE TO RELATED APPLICATIONS

This application claims the benefit under 35 U.S.C. §119 (e) of U.S. Provisional Application No. 61/585,542 filed on Jan. 11, 2012, and U.S. Provisional Application No. 61/587,546 filed on Jan. 17, 2012, the disclosures of each of which are herein incorporated by reference in their entirety.

REFERENCE TO GOVERNMENT SUPPORT

This invention was made with government support under a grant from the National Institute of Environmental Health Sciences, grant number ES04705 and under Contract No. DE-AC02-05CH11231 awarded by the U.S. Department of Energy. The government has certain rights in this invention.

INTRODUCTION

Mercury is a neurotoxic global pollutant. The long lifetime of mercury in the atmosphere (>1 year) allows long-range transport, limiting local emission controls from protecting their environments. Policy makers are working towards a worldwide effort similar to the sulfur dioxide or CFC regulations of the 20th century. Anticipating a global policy, the European Commission began a five-year project called the Global Mercury Observation System (GMOS) to create a coordinated global network adequate for improving models and making policy recommendations. CMOS would expand on the regional efforts made in North America (e.g., the Mercury Deposit Network and North American Airborne Mercury Experiment) and the independent observations made around the world. A preliminary assessment by CMOS indicates there are gaps in emissions monitoring and in the spatial coverage of environmental observations, such as in the southern hemisphere. Current air monitors utilizing cold-vapor atomic fluorescence spectroscopy (CVAFS), with a mercury trap for pre-concentration are used to detect the global ambient background of mercury, but are costly, high maintenance, and require high power. Pre-concentration of trace mercury vapor in samples from the ambient environment is required to produce samples with mercury in detectable amounts. Lack of an inexpensive, stand alone, low power, low maintenance mercury sensor is a technical issue confronting the CMOS.

SUMMARY

A mercury detection system that includes a flow cell having a mercury sensor, a light source and a light detector is provided. The mercury sensor includes a transparent substrate and a submonolayer of mercury absorbing nanoparticles, e.g., gold nanoparticles, on a surface of the substrate. Methods of determining whether mercury is present in a sample using the mercury sensors are also provided. The subject mercury detection systems and methods find use in a variety of different applications, including mercury detecting applications.

Embodiments of the present disclosure provide a mercury detection system which includes a flow cell that includes a mercury sensor, where the mercury sensor includes a transparent substrate and a submonolayer of gold nanoparticles on a surface of the substrate. The mercury detection system also includes a light source and a light detector.

In some embodiments of the mercury detection system, the submonolayer has a density of $5 \times 10^{12}$ gold nanoparticles/cm$^2$ or less.

In some embodiments of the mercury detection system, the gold nanoparticles are spherical.

In some embodiments of the mercury detection system, the gold nanoparticles have an elongated shape. In some embodiments, the gold nanoparticles have an aspect ratio of 2 or more. In some embodiments, the gold nanoparticles have a surface area to volume ratio of 0.2 or more.

In some embodiments of the mercury detection system, the nanoparticles are substantially free of a surface coating.

In some embodiments, the mercury detection system also includes a gas source in communication with the flow cell and configured to provide a flow of a gas through the flow cell.

In some embodiments of the mercury detection system, the light source is a visible light source. In some embodiments of the mercury detection system, the light detector is a UV-Vis photodetector.

In some embodiments of the mercury detection system, the system is configured to detect mercury vapor at a concentration of 100 µg/m$^3$ or less.

Embodiments of the present disclosure provide a method for determining whether mercury is present in a sample. The method includes contacting a sample to a mercury sensor, directing light from a light source to the sample-contacted mercury sensor, and detecting a change in visible light absorbance of the gold nanoparticles to determine whether mercury is present in the sample. The mercury sensor includes a transparent substrate and a submonolayer of gold nanoparticles on a surface of the substrate.

In some embodiments of the method, the contacting includes flowing a gaseous sample through a flow cell that includes the mercury sensor.

In some embodiments, the method also includes quantifying the amount of mercury in the sample. In some embodiments, the quantifying includes determining the amount of mercury in the sample based on the rate of change in the localized surface plasmon resonance wavelength of the gold nanoparticles. In some embodiments, the quantifying includes determining the amount of mercury in the sample based on the rate of change of the absorbance (A) at wavelength ($\lambda$) bands of greatest slope (dA/d$\lambda$) near the localized surface plasmon resonant peak.

In some embodiments of the method, the contacting includes flowing a gaseous sample through a nozzle perpendicular to the mercury sensor.

In some embodiments, the method also includes contacting the sensor with water vapor before contacting the sample to the sensor.

In some embodiments, the method also includes regenerating the mercury sensor. In some embodiments, the regenerating includes heating the mercury sensor.

DETAILED DESCRIPTION

Figure 1:
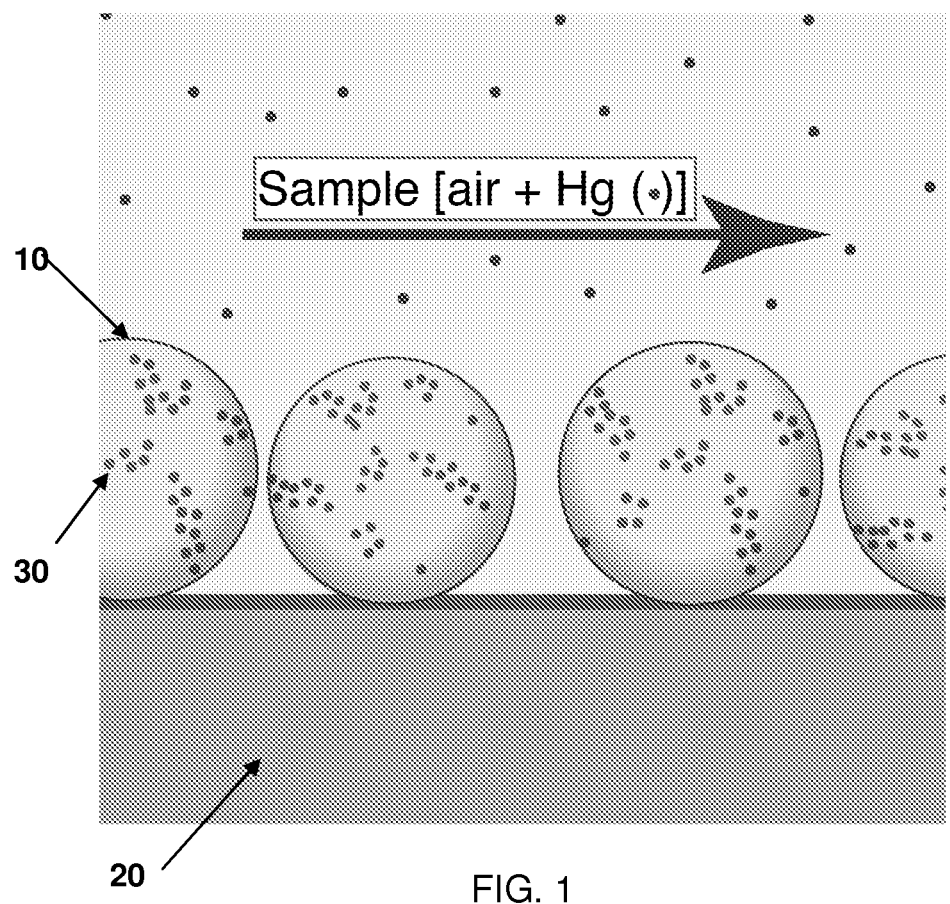
FIG. 1 shows a schematic of a mercury detection system, according to embodiments of the present disclosure.

A mercury detection system that includes a flow cell having a mercury sensor, a light source and a light detector is provided. The mercury sensor includes a transparent substrate and a submonolayer of mercury absorbing nanoparticles, e.g., gold nanoparticles, on a surface of the substrate. Methods of determining whether mercury is present in a sample using the mercury sensors are also provided. The subject mercury detection systems and methods find use in a variety of different applications, including mercury detecting applications.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the present disclosure, aspects of embodiments of the mercury detection systems are described first in greater detail. Following this description, a description of methods of determining whether mercury is present in a sample is provided. Finally, a review of the various applications in which the systems and methods may find use is provided.

Systems

Systems of the present disclosure are mercury detection systems that are configured to determine whether mercury is present in a sample. In certain embodiments, the mercury detection system includes a mercury sensor. The mercury sensor includes a substrate with a layer of nanoparticles on a surface of the substrate. By "nanoparticles" is meant particles that have an average size in the nanometer size range, such as an average size ranging from 1 nm to 1000 nm. By "average size" is meant the statistical mean average size. For example, nanoparticles of the present disclosure may have an average size ranging from 1 nm to 1000 nm, including from 1 nm to 750 nm, or from 1 nm to 500 nm, or from 1 nm to 250 nm, or from 1 nm to 100 nm, such as from 10 nm to 75 nm. In some instances, the nanoparticles may have a smaller average size ranging from 1 nm to 100 nm, or 1 nm to 75 nm, such as from 1 nm to 50 nm, including from 1 nm to 25 nm, or from 1 nm to 10 nm, or from 1 nm to 5 nm, or from 3 nm to 5 nm.

In certain embodiments, the nanoparticles are arranged on the surface of the substrate in a layer of nanoparticles, such as one or more layers of nanoparticles on the surface of the substrate. In some cases, the nanoparticles are arranged in a single layer on the surface of the substrate. A single layer may be a layer that is one-particle thick. For example, the nanoparticles may be arranged in a monolayer on the surface of the substrate. By "monolayer" is meant a single, closely packed layer of nanoparticles on the surface of the substrate. In some cases, the monolayer is substantially continuous, such that there are substantially no gaps between adjacent nanoparticles. For example, nanoparticles in a monolayer may be in contact with surrounding adjacent nanoparticles. In certain embodiments, the nanoparticles are arranged in a submonolayer on the surface of the substrate. By "submonolayer" is meant a layer of nanoparticles on the surface of the substrate, where the layer is discontinuous in one or more regions. For example, nanoparticles in a submonolayer may be dispersed such that the nanoparticles do not substantially contact surrounding nanoparticles. In some instances, a submonolayer may include one or more groupings (e.g., islands) of nanoparticles surrounded by one or more regions of the substrate surface. In certain cases, the groupings of nanoparticles may be dispersed such that the groupings of nanoparticles do not substantially contact surrounding groupings of nanoparticles. In other cases, the groupings of nanoparticles may be interconnected by one or more bridges of nanoparticles to form a substantially contiguous submonolayer on the surface of the substrate.

In certain embodiments, the layer of nanoparticles on the substrate surface has a density of $10 \times 10^{12}$ nanoparticles/cm$^2$ or less, such as $9 \times 10^{12}$ nanoparticles/cm$^2$ or less, or $8 \times 10^{12}$ nanoparticles/cm$^2$ or less, or $7 \times 10^{12}$ nanoparticles/cm$^2$ or less, including $6 \times 10^{12}$ nanoparticles/cm$^2$ or less, or $5 \times 10^{12}$ nanoparticles/cm$^2$ or less, or $4 \times 10^{12}$ nanoparticles/cm$^2$ or less, or $3 \times 10^{12}$ nanoparticles/cm$^2$ or less, or $2 \times 10^{12}$ nanoparticles/cm$^2$ or less, or $1 \times 10^{12}$ nanoparticles/cm$^2$ or less, or $9 \times 10^{11}$ nanoparticles/cm$^2$ or less, or $8 \times 10^{11}$ nanoparticles/cm$^2$ or less, or $7 \times 10^{11}$ nanoparticles/cm$^2$ or less, or $6 \times 10^{11}$ nanoparticles/cm$^2$ or less, or $5 \times 10^{11}$ nanoparticles/cm$^2$ or less, or $4 \times 10^{11}$ nanoparticles/cm$^2$ or less, or $3 \times 10^{11}$ nanoparticles/cm$^2$ or less, or $2 \times 10^{11}$ nanoparticles/cm$^2$ or less, or $1 \times 10^{11}$ nanoparticles/cm$^2$ or less.

In certain embodiments, nanoparticles of the mercury sensor are made of a material that adsorbs mercury. For instance, the nanoparticles may be made of a material, such as a metal. In some cases, the metal is a metal that adsorbs mercury. For example, the metal may be a metal capable of adsorbing mercury from a surrounding sample fluid, such as mercury vapor in a gaseous sample, or mercury in a liquid sample. In certain embodiments, the metal is gold. As such, in some embodiments, the mercury sensor includes gold nanoparticles on the surface of the substrate. As discussed above, the gold nanoparticles may be arranged in a monolayer or a submonolayer on the surface of the substrate.

In certain embodiments, the nanoparticles have a shape that is substantially symmetrical. For example, the nanoparticles may be substantially spherical. By substantially spherical is meant that the nanoparticles have a three-dimensional shape that approximates a sphere. In some instances, the spherical nanoparticles have an average diameter ranging from 1 nm to 100 nm, or 1 nm to 75 nm, such as from 1 nm to 50 nm, including from 1 nm to 25 nm, or from 1 nm to 10 nm, or from 1 nm to 5 nm, or from 3 nm to 5 nm. In certain embodiments, the spherical nanoparticles have an average diameter ranging from 3 nm to 5 nm. By "average diameter" is meant the statistical mean average diameter. In some cases, the spherical nanoparticles have a surface area to volume ratio of 0.1 or more, such as 0.2 or more, including 0.3 or more, or 0.4 or more, or 0.5 or more, or 0.6 or more, or 0.7 or more, or 0.8 or more, or 0.9 or more, or 1.0 or more, or 1.2 or more, or 1.4 or more, or 1.6 or more, or 1.8 or more, or 2 or more, or 2.5 or more, or 3 or more, or 3.5 or more, or 4 or more, or 4.5 or more, or 5 or more.

In certain embodiments, the nanoparticles have a shape that is an elongated shape. By elongated shape is meant a particle that has a length that is longer than its width. For instance, an elongated nanoparticle may have an aspect ratio, which is the ratio of the length of the nanoparticle to the width of the nanoparticle. In certain embodiments, the elongated nanoparticle has an aspect ratio greater than 1, such as 1.5 or more, including 2 or more, or 2.5 or more, or 3 or more, or 3.5 or more, or 4 or more, or 4.5 or more, or 5 or more, or 6 or more, or 7 or more, or 8 or more, or 9 or more, or 10 or more. For example, the elongated nanoparticle may have an aspect ratio of 2 or more. In certain embodiments, the elongated nanoparticle has an aspect ratio ranging from 1 to 10, such as from 1 to 7, including from 1 to 5, or from 2 to 5, or from 2.5 to 4.5.

In some embodiments, the elongated nanoparticle has a length ranging from 1 nm to 1000 nm, including from 1 nm to 750 nm, or from 1 nm to 500 nm, or from 1 nm to 250 nm, or from 1 nm to 100 nm, such as from 10 nm to 75 nm, or from 25 nm to 75 nm, or from 50 nm to 75 nm. For instance, the elongated nanoparticle may have a length ranging from 50 nm to 75 nm, such as a length of 60 nm. In some embodiments, the elongated nanoparticle has a width ranging from 1 nm to 1000 nm, including from 1 nm to 750 nm, or from 1 nm to 500 nm, or from 1 nm to 250 nm, or from 1 nm to 100 nm, such as from 10 nm to 75 nm, or from 10 nm to 50 nm. For instance, the elongated nanoparticle may have a length ranging from 10 nm to 50 nm, such as a width of 20 nm.

In some cases, the elongated nanoparticle has a surface area to volume ratio of 0.1 or more, such as 0.2 or more, including 0.3 or more, or 0.4 or more, or 0.5 or more, or 0.6 or more, or 0.7 or more, or 0.8 or more, or 0.9 or more, or 1.0 or more, or 1.2 or more, or 1.4 or more, or 1.6 or more, or 1.8 or more, or 2 or more, or 2.5 or more, or 3 or more, or 3.5 or more, or 4 or more, or 4.5 or more, or 5 or more. For example, the elongated nanoparticle may have a surface area to volume ratio of 0.2 or more. In some instances, the elongated nanoparticle has a surface are to volume ratio ranging from 0.1 to 3, such as from 0.1 to 2, including from 0.1 to 1, or from 0.1 to 0.5, or from 0.1 to 0.4, or from 0.1 to 0.3, or from 0.2 to 0.3.

In some cases, the elongated nanoparticle has an elongated shape, such as, but not limited to, a cylinder (e.g., a nanocylinder) or a rod (e.g., a nanorod). In some embodiments, the elongated nanoparticle has a cross-sectional profile (e.g., a cross section that intersects the longitudinal axis of the elongated nanoparticle) that has a shape that is substantially circular. Other cross-sectional profiles are possible, such as, but not limited to, an elongated nanoparticle that has a cross-sectional profile in the shape of an ellipse, a rectangle, a square, an irregular shape, and the like.

In certain embodiments, the nanoparticles are substantially free of a surface coating. Nanoparticles that are substantially free of a surface coating are configured such that the exterior surface of the nanoparticle is directly exposed to the surrounding environment. For example, during fabrication of the mercury sensor, the nanoparticles may be washed to remove any surface coating present of the nanoparticles. The surface coating may be removed either before or after the nanoparticles are attached to the surface of the substrate of the mercury sensor. In some cases, the exterior surfaces of the nanoparticles that are exposed to the surrounding environment (including the sample to be tested for the presence of mercury) are substantially free of a surface coating.

As described above, the mercury sensor of embodiments of the present disclosure includes a substrate. Nanoparticles are attached to the substrate to form the mercury sensor. The nanoparticles may be attached to the surface of the substrate through covalent bonds or non-covalent interactions, such as, but not limited to, ionic bonds, hydrophobic interactions, hydrogen bonds, van der Waals forces (e.g., London dispersion forces), dipole-dipole interactions, and the like. In certain embodiments, the nanoparticles are attached to one surface of the substrate. For example, the nanoparticles may be attached to one side of a planar substrate. In some cases, the opposing side of the substrate is substantially free of nanoparticles, such that only one surface of the substrate has nanoparticles attached. In other instances, where an optical fiber is used as the substrate (as described in more detail below), the nanoparticles may be attached to the exterior surface of the optical fiber. For instance, the nanoparticles may be attached to a portion of the optical fiber where the exterior surface is exposed (e.g., substantially free of surface coatings).

In certain embodiments, the substrate is substantially transparent. By transparent is meant that light is transmitted through the substrate. In some embodiments, the substrate is substantially planar. In certain embodiments, the mercury sensor can have an area of 10 cm$^2$ or less, such as 5 cm$^2$ or less, including 3 cm$^2$ or less, or 1 cm$^2$ or less, including 50 mm$^2$ or less, or 20 mm$^2$ or less, such as 10 mm$^2$ or less, or 5 mm$^2$ or less, or even smaller. For example, the mercury sensor may have dimensions in the range of 10 μm×10 μm to 10 mm×10 mm, including dimensions of 10 mm×10 mm or less, such as 5 mm×5 mm or less, for instance 1 mm×1 mm or less, or 100 μm×100 μm or less, or 50 μm×50 μm or less. In some instances, the substrate is composed of a transparent material, such as, but not limited to, glass (e.g., silica glass), quartz, and the like.

In certain embodiments, the substrate is an optical fiber (i.e., a fiber optic cable). The optical fiber may have a diameter of 1 mm or less, such as 750 μm or less, including 500 μm or less, or 250 μm or less, or 100 μm or less, or 50 μm or less, or 25 μm or less, or 10 μm or less or 5 μm or less. In some instances, the optical fiber has a diameter of 750 μm or less, such as a diameter of 600 μm. In some instances, the optical fiber is composed of a transparent material, such as, but not limited to, glass (e.g., silica glass), and the like.

In certain embodiments, the mercury detection system includes a flow cell. The flow cell may be configured to carry a flow of a fluid through the mercury detection system. For example, the flow cell may be configured to carry a flow of a gas (e.g., a gaseous sample) through the mercury detection system. In other embodiments, the flow cell may be configured to carry a flow of a sample liquid through the mercury detection system. The mercury sensor may be positioned in the flow cell, such that the surface of the mercury sensor (e.g., the surface of the mercury sensor with the nanoparticles) is in contact with the flow of the gas flowing through the system. For instance, the flow cell may be configured such that the mercury sensor is positioned on one side of the interior of the flow cell. In some embodiments, the flow cell is configured such that the gas flows across (e.g., substantially parallel to) the surface of the mercury sensor as the gas flows through the flow cell. For example, the system may include a gas source in communication with the flow cell. The gas source may be configured to provide a flow of a gas through the flow cell. The gas may be a gaseous sample to be tested for the presence of mercury, such as a gaseous sample suspected of containing mercury.

In other embodiments, the flow cell may be configured such that the flow of the incoming gas is substantially perpendicular to the surface of the mercury sensor. For instance, the flow cell may include a nozzle arranged substantially perpendicular to the surface of the mercury sensor. Gas from the gas source may flow through the nozzle and contact the mercury sensor substantially perpendicularly to the surface of the mercury sensor. In some cases, this perpendicular configuration may facilitate an increase in the sensitivity of the mercury sensor.

In certain embodiments, the mercury detection system includes a light source. The light source may be configured to direct light from the light source to the mercury sensor. For example, the light source may be configured to direct light from the light source to the transparent substrate of the mercury sensor. As described above, the transparent substrate may have one surface with nanoparticles attached and the opposing surface may be substantially free of nanoparticles. In these embodiments, the light source may be configured to direct light from the light source to the side of the transparent substrate opposite the side of the substrate with the nanoparticles. Stated another way, the light source may be configured to direct light from the light source to the side of the transparent substrate that is substantially free of nanoparticles.

In certain embodiments, the light source is configured to direct light to the mercury sensor at an angle. The angle may be measured as the angle between the incident light and a line perpendicular to the surface of the substrate. In some instances, the angle is from 0 to 90 degrees, such as from 15 to 75 degrees, including from 30 to 60 degrees.

In certain embodiments, the light source is a visible light source. The visible light source may be configured to emit light in the visible range of the electromagnetic spectrum. Other embodiments of the light source may be configured to emit light in the ultraviolet (UV) range, or the infrared range of the spectrum. In embodiments of the light source configured to emit light on the visible range of the spectrum, the light source may include, but is not limited to, a lamp (e.g., a halogen lamp), a laser, and the like.

In certain embodiments, the mercury detection system includes a detector. In some instances, the detector is a light detector. The light detector may be configured to detect light emitted from the mercury sensor in the visible range of the electromagnetic spectrum. In some cases, the detector is configured to detect light emitted from the mercury sensor in the ultraviolet range of the electromagnetic spectrum. In some cases, the detector is configured to detect light emitted from the mercury sensor in the infrared range of the electromagnetic spectrum. In some cases, the detector is configured to detect light emitted from the mercury sensor in more than one range of the electromagnetic spectrum, such as in the UV and visible, or the visible and infrared, or the UV, visible and infrared ranges of the spectrum. In certain embodiments, the detector is a light detector, such as, but not limited to a UV-Vis photodetector, a spectrometer, and the like.

The detector may be configured to detect emissions and/or reflected light from the mercury sensor, such as electromagnetic emissions from the mercury sensor and/or light from the light source reflected by the mercury sensor. For example, the detector may be configured to detect light from the light source reflected by the mercury sensor. In some instances, the system is configured to detect a minimum in the light reflected by the mercury sensor. Stated another way, the system may be configured to detect a maximum in the absorbance (e.g., a local maximum in the absorbance). In some cases, the system is configured to detect a wavelength at which a maximum in absorbance occurs (i.e., a peak localized surface plasmon resonance (LSPR) wavelength).

In certain embodiments, the mercury detection system is configured to determine whether mercury is present is a sample based on the localized surface plasmon resonance (LSPR) wavelength of the nanoparticles. For example, the system may be configured to detect a peak LSPR wavelength (e.g., the LSPR wavelength at which a local maximum in absorbance occurs). In some cases, the peak LSPR wavelength may provide a qualitative indication of whether mercury is present or absent in a sample. For instance, the system may be configured to detect a shift or a change in the peak LSPR wavelength (e.g., as compared to a baseline or control measurement in the absence of mercury). In some cases, a shift in the peak LSPR wavelength is an indication of the presence of mercury in the sample. Without being limited to any particular theory, as a sample containing mercury contacts the mercury sensor, mercury from the sample may be adsorbed onto the nanoparticles (e.g., gold nanoparticles) of the mercury sensor. The adsorption of mercury onto the nanoparticles may cause the peak LSPR wavelength to shift from its original wavelength (e.g., the peak LSPR wavelength in the absence of mercury). As such, a shift in the peak LSPR wavelength may indicate the presence of mercury in the sample. For instance, the shift in the peak LSPR wavelength may be proportional to the mass fraction of mercury adsorbed by the nanoparticles of the sensor and can be used as the basis of quantification of mercury concentration in the sample.

In some instances, the shift in the peak LSPR wavelength is a blue shift. By blue shift is meant a decrease in the peak LSPR wavelength (e.g., a change in the peak LSPR wavelength to a shorter wavelength). In certain cases, the shift in the peak LSPR wavelength is 0.5 nm or more, such as 1 nm or more, including 1.5 nm or more, or 2 nm or more, or 2.5 nm or more, or 3 nm or more, or 3.5 nm or more, or 4 nm or more, or 4.5 nm or more, or 5 nm or more, or 5.5 nm or more, or 6 nm or more, or 6.5 nm or more, or 7 nm or more, or 7.5 nm or more, or 8 nm or more, or 8.5 nm or more, or 9 nm or more, or 9.5 nm or more, or 10 nm or more.

In certain embodiments, the sensitivity of the system depends on the surface area to volume (SA:V) ratio of the nanoparticles of the mercury sensor. For example, the shift in the peak LSPR wavelength may depend on the SA:V ratio of the nanoparticles. In some instances, an increase in the SA:V ratio of the nanoparticles increases the magnitude of the shift in the peak LSPR wavelength for a given concentration of mercury in a sample.

In certain embodiments, the system is configured to detect a shift rate of the peak LSPR wavelength (e.g., the change in the peak LSPR wavelength over time). In some instances, the shift rate provides a quantitative indication of the concentration of the mercury in the sample. For example, the shift rate may be linearly dependent on the concentration of mercury in the sample. In certain instances, the shift rate may be 0.1 nm/min or more, such as 0.2 nm/min or more, including 0.3 nm/min or more, or 0.4 nm/min or more, or 0.5 nm/min or more, or 0.6 nm/min or more, or 0.7 nm/min or more, or 0.8 nm/min or more, or 0.9 nm/min or more, or 1 nm/min or more, or 1.2 nm/min or more, or 1.4 nm/min or more, or 1.6 nm/min or more, or 1.8 nm/min or more, or 2 nm/min or more, or 2.5 nm/min or more, or 3 nm/min or more, or 3.5 nm/min or more, or 4 nm/min or more, or 4.5 nm/min or more, or 5 nm/min or more.

In certain embodiments, the system is configured to detect a change in the percent slope over time (e.g., the change in the peak LSPR wavelength over time as a percentage of the initial peak LSPR wavelength). In some instances, the percent slope provides a quantitative indication of the concentration of the mercury in the sample. For example, the percent slope may be linearly dependent on the concentration of mercury in the sample. In certain instances, the percent slope may be 0.01% change/min or more, such as 0.02% change/min or more, including 0.03% change/min or more, or 0.04% change/min or more, or 0.05% change/min or more, or 0.06% change/min or more, or 0.07% change/min or more, or 0.08% change/min or more, or 0.09% change/min or more, or 0.1% change/min or more, or 0.15% change/min or more, or 0.2% change/min or more, or 0.25% change/min or more, or 0.3% change/min or more, or 0.35% change/min or more, or 0.4% change/min or more, or 0.45% change/min or more, or 0.5% change/min or more.

In certain embodiments, the system is configured to detect mercury vapor at a concentration of 100 $\mu g/m^3$ or less. For example, the system may be configured to detect mercury vapor at a concentration of (e.g., the system may be configured to have a limit of detection of) 100 $\mu g/m^3$ or less, such as 75 $\mu g/m^3$ or less, including 50 $\mu g/m^3$ or less, or 25 $\mu g/m^3$ or less, or 10 $\mu g/m^3$ or less, or 5 $\mu g/m^3$ or less, or 1 $\mu g/m^3$ or less, or 750 $ng/m^3$ or less, or 500 $ng/m^3$ or less, or 250 $ng/m^3$ or less, or 100 $ng/m^3$ or less, or 75 $ng/m^3$ or less, or 50 $ng/m^3$ or less, or 25 $ng/m^3$ or less, or 10 $ng/m^3$ or less, or 5 $ng/m^3$ or less, or 1 $ng/m^3$ or less. In certain embodiments, because the system is configured to have a low limit of detection as described above, the system may detect mercury in samples where the sample is directly analyzed by the system. For instance, the sample may be obtained and analyzed by the system directly with no preconditioning (e.g., concentration) of the sample prior to analysis.

In certain embodiments, the system further includes a heat source. The heat source may be configured to facilitate regeneration of the mercury sensor. For example, the heat source may be configured to heat the mercury sensor. In some instances, heating the mercury sensor may facilitate the release of adsorbed mercury from the mercury sensor, which may prepare the mercury sensor for subsequent use in testing one or more additional samples for the presence of mercury. In some cases, the heat source includes, but is not limited to, a heating coil, a heating lamp, and the like. In some embodiments, the heat source is configured to heat the mercury sensor to a temperature of 100° C. or more, such as 110° C. or more, or 120° C. or more, or 130° C. or more, or 140° C. or more, or 150° C. or more, or 160° C. or more, or 170° C. or more, or 180° C. or more, or 190° C. or more, or 200° C. or more. In some cases, the heat source is configured to heat the mercury sensor to a temperature ranging from 100° C. to 200° C., such as from 100° C. to 190° C., including from 100° C. to 180° C., or from 110° C. to 170° C., or from 120° C. to 160° C.

An embodiment of a mercury detection system is shown in FIG. 1. As shown in FIG. 1, nanoparticles (e.g., gold nanoparticles) 10 are attached to a surface of a substrate 20. During use, mercury 30 from a sample is adsorbed onto the nanoparticles 10.

Methods

Aspects of embodiments of the present disclosure include a method of determining whether mercury is present is a sample. The method includes contacting a sample to a mercury sensor of a mercury detection system to produce a sample-contacted mercury sensor. Aspects of the mercury sensor and mercury detection system are described above. In some instances, the contacting includes directing a flow of a sample to contact the mercury sensor. For gaseous samples, directing the flow of a sample may include directing the gaseous sample through a flow cell to contact a mercury sensor in the flow cell. The gas may be a gaseous sample to be tested for the presence of mercury, such as a gaseous sample suspected of containing mercury. The flow of the gaseous sample may be directed to contact the surface of the mercury sensor that has the nanoparticles attached. In certain cases, the directing includes directing the flow of the sample across (e.g., substantially parallel to) the surface of the mercury sensor. In other embodiments, the directing includes directing the flow of the sample to the mercury sensor such that the flow of the sample is substantially perpendicular to the surface of the mercury sensor.

In certain embodiments, the method includes directing light from a light source to the sample-contacted mercury sensor. Light from the light source may be directed to the sample-contacted mercury sensor. In some cases, the light is directed to a surface of the mercury sensor opposite the surface of the mercury sensor that has the nanoparticles attached. For example, the mercury sensor may include a transparent substrate with one surface that includes a layer (e.g., a sub-monolayer) of nanoparticles attached. In these embodiments, the method includes directing light from the light source to a surface of the transparent substrate opposite the surface of the substrate with the nanoparticles.

Embodiments of the method also include detecting light emitted and/or reflected from the mercury sensor. In some instances, the method includes detecting changes in visible light absorption of the nanoparticles (e.g., gold nanoparticles) to determine whether mercury is present in the sample. For example, the method may include detecting changes in the wavelength at which a maximum (e.g., a local maximum) in the visible light absorption of the nanoparticles occurs, such as detecting changes in the LSPR wavelength at which a maximum in the visible light absorption of the nanoparticles occurs. As described above, this shift in the peak LSPR wavelength may provide an indication of the presence of mercury in the sample.

In certain cases, the method further includes quantifying the amount of mercury in the sample. For example, the quantifying may include determining the amount of mercury in the sample based on the rate of change in the localized surface plasmon resonance wavelength of the nanoparticles. As described above, the rate of change (i.e., the shift rate, or change in the peak LSPR wavelength over time) may be linearly dependent on the concentration of mercury in the sample. As such, by determining the shift rate of the peak LSPR wavelength based on the detected light, the concentration of mercury in the sample may be determined.

In certain embodiments, quantifying the amount of mercury in the sample includes determining the amount of mercury in the sample based on the rate of change of the absorbance (A) at wavelength ($\lambda$) bands of greatest slope ($dA/d\lambda$) near the localized surface plasmon resonant peak. For example, the method may include detecting the LSPR resonant peak (e.g., the local maximum in absorbance) over time. The method may further include determining the change in absorbance as the wavelength changes due to shifts in the LSPR wavelength. In some instances, the rate of change of the absorbance at wavelengths with the greatest slope is correlated to the concentration of mercury in the sample. As such, by determining the rate of change of the absorbance, the concentration of mercury in the sample may be determined.

In certain embodiments of the method, the contacting includes flowing a gaseous sample through a flow cell comprising the mercury sensor. In some instances, the gaseous sample has a flow rate of 1 L/min or more, such as 20 L/min or more, or 50 L/min or more, or 100 L/min or more, or 200 L/min or more.

In some instances, the method further includes regenerating the mercury sensor. For example, the regenerating may include heating the mercury sensor. Regenerating the mercury sensor may facilitate reuse of the same sensor two or more times to determine whether mercury is present in a sample (e.g., the same sample or different samples). For instance, the same sensor may be regenerated and reused 2 or more times, or 5 or more times, or 10 or more times, including 20 or more times, or 50 or more times, or 100 or more times. In some cases, the mercury sensor can be regenerated multiple times with no significant decrease in sensitivity.

In certain embodiments, the method includes contacting the mercury sensor with water (e.g., water vapor) before contacting the sample to the mercury sensor. Contacting the mercury sensor with water before contacting the sample to the mercury sensor may facilitate a reduction in signal interference and/or noise due to changes in humidity.

Utility

Mercury detection systems and methods as disclosed herein find use in the detection of mercury in a sample. As described above, the sample may be a gaseous sample to be tested for the presence of mercury, such as a gaseous sample suspected of containing mercury. As such, systems and methods as disclosed herein find use in the detection of mercury in a gaseous sample. For example, mercury detection systems and methods as disclosed herein find use in environmental, occupational, and regulatory measurements of mercury. Samples may include, but are not limited to, samples obtained from the surrounding environment, samples obtained from emission gases (e.g., emission gases from combustion engines), samples obtained from emissions from manufacturing and/or laboratory processes, and the like. For instance, the mercury detection systems and methods find use in the monitoring of ambient mercury concentrations around the world, such as for the Global Mercury Observation System (GMOS).

Mercury detection systems and methods as disclosed herein also find use in continuous emission monitoring systems (CEMS). For example, the systems and methods disclosed herein may be used to detect mercury in samples analyzed by CEMS. In some instances, the systems and methods provide an increase in sensitivity as compared to conventional mercury detection systems, and may also provide a reduction in cross-sensitivity to other analytes.

In certain embodiments, the mercury detection systems and methods find use in portable mercury detection. Gold nanoparticle sensors as described herein that use visible light absorbance spectroscopy may facilitate a reduction in the size and cost of mercury detection systems. In addition, in some instances, the systems and methods disclosed herein require less power and maintenance than conventional systems such as atomic absorption/fluorescence spectroscopy.

The following examples are put forth so as to provide those of ordinary skill in the art with a complete disclosure and description of how to make and use the embodiments disclosed herein, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Averages are calculated as the statistical mean average.

EXAMPLES

Example 1

Nanoparticle Film Preparation

Quartz, diced in 9 mm squares, acted as the transparent substrate for the nanoparticle film. Before use, the quartz surfaces were cleaned in piranha solution for 15 minutes, rinsed in water (18.2 MΩ, Millipore, Billerica, Mass.) and ethanol, and dried in nitrogen. Non-polar soluble 5 nm gold nanoparticles (Alfa Aesar, Ward Hill, Mass.) were suspended in chloroform and deposited, dropwise, onto the water surface held by a Teflon Langmuir-Blodgett trough (Nima, Espoo, Finland). After 30 minutes, the film was compressed, using the motorized Teflon barrier, to 10-30 mN/m$^2$ surface pressure. The particle monolayer formed while floating on the aqueous subphase, controlled by the uniaxial compression of the trough surface area. The substrate dipper then drew the submerged quartz chips and transmission electron microscopy (TEM) grids (silicon nitride, Ted Pella, Redding, Calif.) through the floating nanoparticle layer, fixing the particles to the substrate surfaces. Selected nanoparticle films were plasma cleaned (Harrick, Ithaca, N.Y.) for 1 minute at high power in oxygen gas at 300 mTorr.

Film Characterization

TEM imaging (H-7650, Hitachi, Tokyo, Japan) and UV-Vis absorption spectroscopy (HR4000, Ocean Optics, Dunedin, Fla.) provided characterization of the particle films. A Lorentzian curve, fitted to the recorded spectra using Matlab, located the peak wavelength of the localized surface plasmon resonance (LSPR) with a resolution of 0.1 nm.

Sample Bag Method

Initial exposures to mercury vapor employed a Teflon sample bag (SKC, Eighty Four, Pa.) with a controlled dilution of saturated mercury vapor in clean air (Zero Air, AirGas, Sacramento, Calif.). A peristaltic pump drew the sample from the bag over the sensor chip at a constant flow of 15 cc/min. A quartz flow cell (Starna Cells, Atascadero, Calif.) held the sensor chip for in situ recording of the absorbance spectra. This technique was used for samples ranging from 25 to 825 $\mu g_{Hg}/m_{air}^3$.

Regeneration

Heating tape, wrapped about the flow cell and connected to an autotransformer, was used to heat the sensors to regenerate the sensors. A flow of mercury free air through the flow cell (6 liters per minute (LPM)) during heating purged the system. A temperature of 433 K was used for regeneration, which minimized coalescing of the nanoparticles, allowing reuse of the sensor for further measurements.

Permeation Tube Method

Two methods with higher flow rates used a permeation tube to generate a constant concentration of calibration gas. In one method, a sensor was fixed across a 1.25 cm inner-diameter Pyrex tube. The sensor was oriented in a cross-flow geometry to the calibration gas. The collimating lenses and tube were held in a fixed position with the beam perpendicular to the sensor, which allowed observation of a consistent area of the sensor during the absorbance measurements. In the second method, the sensor was held on a mirror surface and exposed to calibration gas impinging from a closely placed nozzle.

A permeation tube in a steady flow of air supplied a constant mercury concentration for the higher flow rates. The emission of Hg from the permeation tube was constant for a given temperature with 60 ng/s emitted at room temperature. For 57 LPM of air flow, the permeation tube system provided 1 $\mu g_{Hg}/m_{air}^3$.

Results and Discussion

Gold nanoparticles were used because gold is a selective and stable mercury adsorbing material and can be grown in a variety of shapes and sizes of nanoparticles. Experiments were performed to determine the most sensitive and stable gold nanoparticle from available shapes and sizes. Shifts in LSPR at saturating concentrations of mercury were greater for smaller nanoparticles. Results from observing the spectral response of individual gold nanoparticles to $\mu g/m^3$ concentrations of mercury in air indicated that the sensitivity was proportional to the surface-area-to-volume ratio. Gold spheres with an average diameter of about 5 nm were used because they have the largest surface-area-to-volume ratio while still having an observable peak in absorbance for an assembled film. Spheres were the minimum surface-area-to-volume ratio shape, but they can be synthesized in smaller sizes than other geometries. In some instances, because spheres are the minimum surface-area-to-volume geometry, they facilitated the shape stability of the spheroid particles. For example, thermodynamics may drive other non-spherical shapes to gradually devolve towards spheres, which results in a reduction in the total surface energy.

The response of a 5 nm gold nanoparticle (AuNP) LSPR to amalgamation was predicted. The LSPR wavelength of bimetallic nanoparticles shifted proportionally to alloying mass fraction. Due to differences in the complex dielectric, a 5 nm Hg particle LSPR wavelength would be 273 nm, which is 240 nm shorter than an AuNP of the same size. The model predicted a shift of 2.4 nm for each percentage increase in the Hg mass fraction, which in the case of the 5 nm sphere was equivalent to 15 atoms of Hg. The model agreed with experimental observations comparing UV-Vis spectra with the measured mass fraction.

The spectral response of an array of AuNP particles was measured using UV-Vis absorbance spectroscopy. Assembly of a nanoparticle film was performed using the Langmuir-Blodgett method. In the Langmuir-Blodgett method, a monolayer or submonolayer of gold nanoparticles may be deposited from the surface of a liquid onto a substrate by immersing (or emersing) the substrate into (or from) the liquid. For example, a submerged substrate may be raised through a floating nanoparticle layer to form a monolayer or submonolayer of nanoparticles on the substrate surface, as described above. Other methods of fabricating a nanoparticle film on the surface of the substrate may be used. For example, a solution that includes the nanoparticles may be contacted with the substrate surface and allowed to dry.

Figure 2:
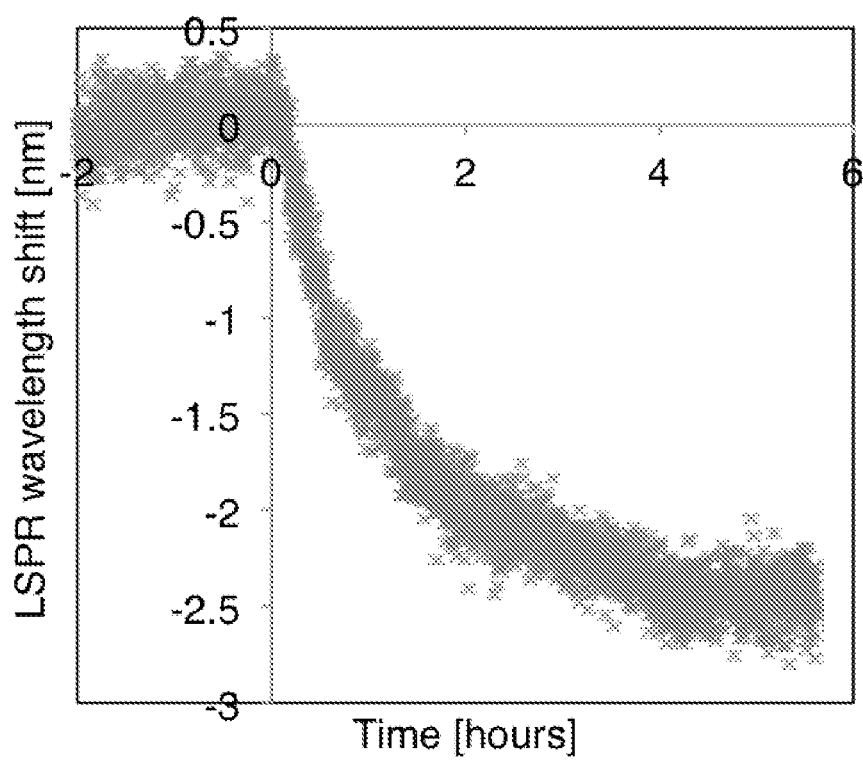
FIG. 2 shows a graph of LSPR wavelength shift (nm) vs. time, according to embodiments of the present disclosure.
Figure 4:
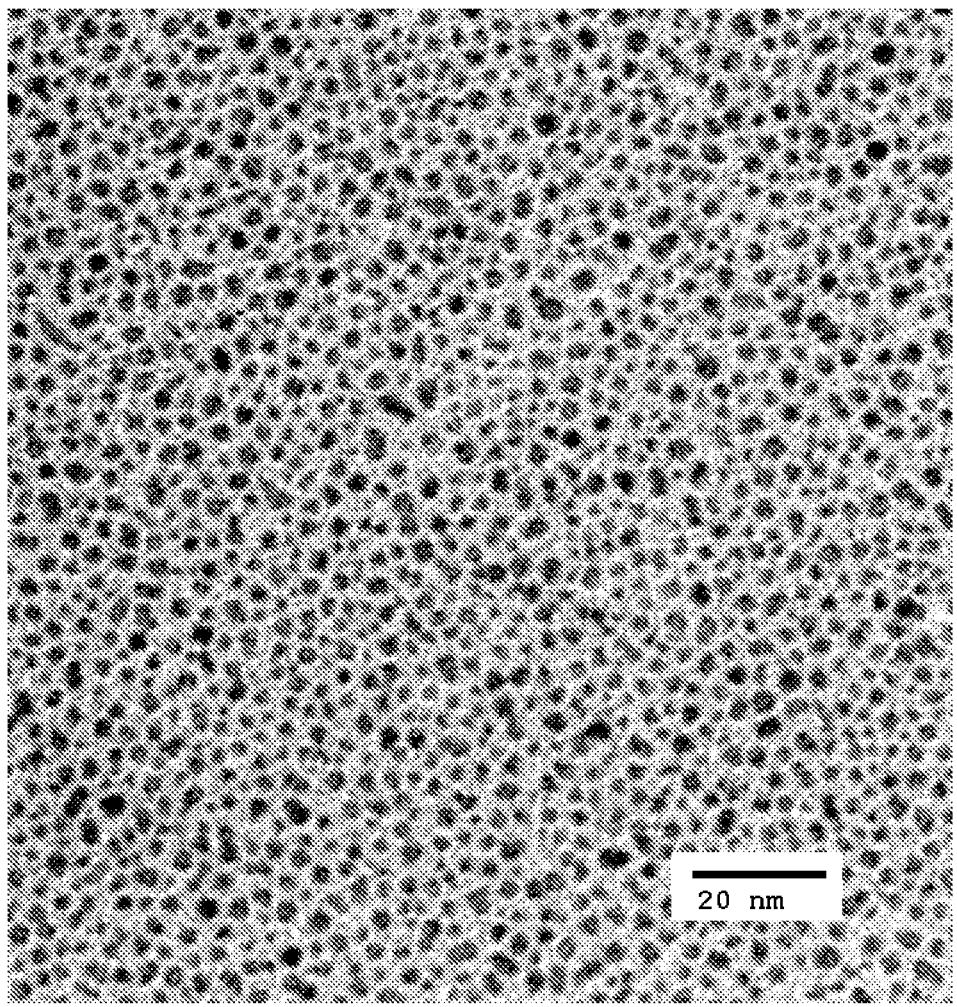
FIG. 4 shows a transmission electron microscopy (TEM) image of gold nanoparticles on a surface of a substrate, according to embodiments of the present disclosure.

TEM images showed the AuNP-films to have a packing density of either 15% or 35% with particles having an average diameter of 4.8 nm (FIG. 4). The packing density was a function of the surface pressure during the Langmuir-Blodgett deposition with lower pressures producing lower surface density films. The two surface pressures tested produced films with $9 \times 10^{11}$ or $2 \times 10^{12}$ particles (7.7 or 18 µg) on each 1 cm$^2$ chip. The close proximity of the particles allowed coupling between neighboring plasmons, driving the resonance to longer wavelengths (isolated particles have a LSPR wavelength of about 520 nm). All films tested in cross-flow exposures to mercury originated from the same Langmuir-Blodgett batch and had an average LSPR wavelength of 551 nm. The less dense films were used in the impinging flow experiments and had a LSPR wavelength of 525 nm. Films exposed to mercury vapor exhibited a blue shift (i.e., a decrease in wavelength) in their LSPR wavelength that slowed as the sensor became saturated (FIG. 2).

Figure 3:
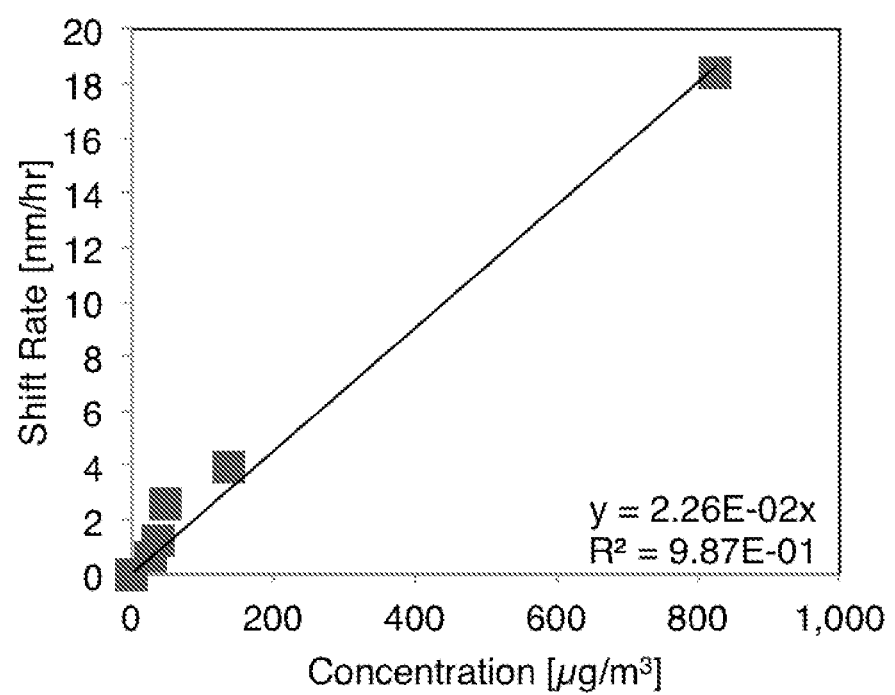
FIG. 3 shows a graph of shift rate (nm/hr) vs. mercury concentration (µg/m$^3$), according to embodiments of the present disclosure.

The response of the AuNPs to mercury vapor related quantitatively to the sample concentration, in a range compatible with environmental observation. Exposed to varying concentrations of Hg in air, the films generated using the Langmuir-Blodgett technique had a higher wavelength shift rate (i.e., blue shifted faster) for higher sample concentrations (FIG. 3). Using a flow rate of 15 cc/min and mercury concentrations ranging from 25 to 825 $\mu g_{Hg}/m_{air}^3$ the film's LSPR shift rate, $v_{LSPR}$, was proportional to the sample concentration. For each $\mu g_{Hg}/m_{air}^3$ increase in sample concentration the $v_{LSPR}$ increased by 0.023 nm/hr. The use of the LSPR shift rate, $v_{LSPR}$, as the metric of choice, rather than the wavelength shift in the LSPR peak, was because the adsorption of vapor phase mercury on the gold surface was controlled by diffusive mass transfer. The mass transfer rate could be accelerated by increasing the bulk flow rate.

For a flat surface introduced into a uniform flow field, flowing parallel to the surface, the mass transfer at the surface for a single dissolved species can be solved analytically if the surface concentration is known and the flow remains laminar. Elemental mercury vapor has a high affinity for gold, with an observed sticking coefficient of approximately one. This allowed the assumption that the mercury vapor concentration at the gold boundary is zero. The solution predicted a mass transfer rate proportional to the square root of the bulk velocity, and linear with the mercury concentration. However, the square root dependence, of adsorption during laminar flow, does not hold for turbulent flows. Empirical observations of the same geometry with turbulent flows showed that the mass transfer rate remained directly proportional to concentration and proportional to the fluid's Reynolds number to a power ranging between 0.8 and 1.

Figure 5:
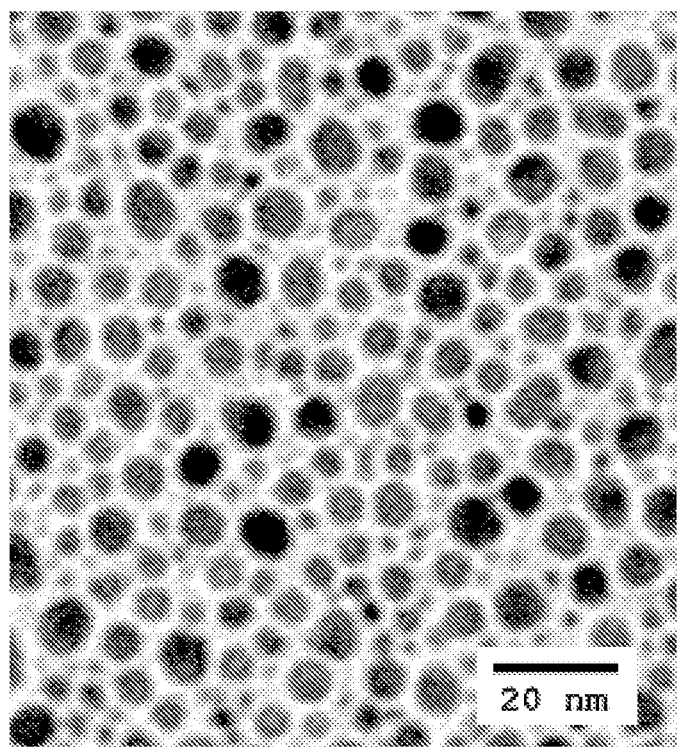
FIG. 5 shows a transmission electron microscopy (TEM) image of gold nanoparticles on a surface of a substrate after heating to 240° C. for 1 hour, according to embodiments of the present disclosure.

Regeneration of the mercury sensor may facilitate continuous measurements and/or remote operation with a reusable mercury sensor. Gold releases mercury when heated, and the gold nanoparticles on the sensor surface can be regenerated one or more times. Experiments were performed that indicated that heating of the gold-mercury amalgam nanoparticle film regenerated the sensitivity by evolution of mercury vapor. The sensor response following an hour at 433 K was consistent, with no degradation in sensor response observed after more than 30 regenerations. Heating to a relatively low temperature (e.g., 433 K) may facilitate preservation of the nanoparticle film morphology, which in turn may facilitate a preservation of the LSPR response. In certain embodiments, melting temperature is size dependent and melting point depression in nanoparticles may make the nanoparticles change morphology at higher temperatures. The melting point depression was nonlinear with particle dimension, which lowered the melting temperature of the 4.8 nm diameter nanoparticles. For example, heating to 513 K for one hour caused the particles to coalesce, forming larger particles (d=8 nm). A TEM image of one such film is shown in FIG. 5. The larger diameter particles showed a 50% reduction in sensitivity to mercury vapor, due in part to a reduction of the surface-area-to-volume ratio.

Figure 6:
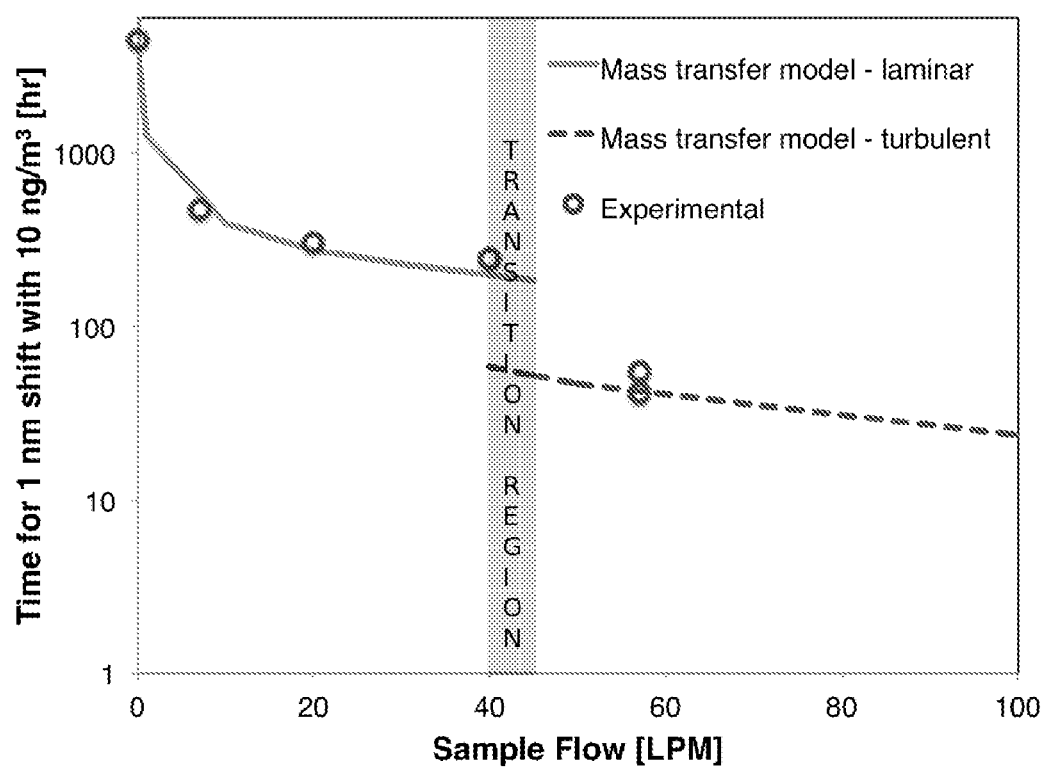
FIG. 6 shows a graph of time for 1 nm LSPR shift with 10 ng/m$^3$ mercury (hr) vs. sample flow (LPM), according to embodiments of the present disclosure.

A single sensor chip was used in a series of exposures and regenerations to test the precision of the method and its agreement with flow rate trends of the mass transfer model. For six runs done with a flow rate and concentration of 20 LPM and 3 µg/m$^3$ mercury, the $v_{LSPR}$ was 1.1 nm/hour on average with a standard deviation of 7%. Increasing the flow rate to 57 LPM with a sample of 1 $\mu g_{Hg}/m_{air}^3$ resulted in a $v_{LSPR}$ of 0.42 nm/hour. For flow rates below 40 LPM the flow in the Pyrex tube flow cell should be laminar. Normalizing $v_{LSPR}$ to a single concentration (10 $ng_{Hg}/m_{air}^3$, e.g., a typical ambient concentration) the experimental data followed a square root dependence on flow rate for flows up to 20 LPM (FIG. 6). For 57 LPM flow in the tube, the fluid was expected to be turbulent (Re=3584) and shifted three times faster than the laminar trend predicted. The time resolution of LSPR sensing of ambient mercury was 48 hours or less, such as 24 hours or less, or 12 hours or less. The time resolution depended on the rate of adsorption, which increased with Reynolds number. At the greatest flow rate tested, 57 LPM, an ambient mercury measurement (10 $ng_{Hg}/m_{air}^3$) took 41 hours to shift 1 nm, but increasing the flow to 200 LPM decreased the time down to below 12 hours.

In certain embodiments, the accuracy of the sensor can be improved by controlling for confounding factors, such as changes in temperature, humidity, etc. Observation of LSPR temperature dependence during the heating and cooling steps of regeneration prompted the use of a thermocouple to monitor the sensor temperature. A linear regression of the LSPR v. temperature data from the hour before exposure allowed normalization of the peak position; the LSPR peak temperature dependence was 1.7 nm/K. Additional confounding effects appeared as a gradual red-shift (i.e., increase in wavelength) of the LSPR for mercury free sample air. This was likely due to other adsorbates, such as water, that increased the index of refraction surrounding the AuNPs causing a shift of the resonance to longer wavelengths. No correction for the red shifts was needed because they were slower than the standard deviation of the sensor response to the tested mercury concentrations.

In certain embodiments, to accelerate mercury adsorption on the sensor, an impinging sample flow geometry was used. In some cases, this geometry increased the mass transfer efficiency, shown by a quicker response in the LSPR of the film for the same concentration and flow rate of mercury vapor sample. When exposed to a 3 µg/m$^3$ sample at 20 LPM, coated films exposed in the impinging geometry were 10 times more sensitive than those exposed in a cross-flow orientation. The peak wavelength shifted 1±0.015 nm/min when exposed to a 3 µg/m$^3$ sample at 20 LPM. These films also displayed a narrower LSPR peak. This resulted in 0.09 nm LSPR wavelength resolution for the Lorentzian curve fitting. Plasma cleaning of the sensor increased the sensitivity an additional 6 fold. The sensitivity to humidity also increased by a factor of 2. To avoid humidity cross sensitivity, the sensor was saturated with humid air before exposing the sensor to the mercury sample. Results indicated that this prevented interference from water vapor in the mercury sample. Using the plasma cleaned sensor, sample concentrations of 100 ng/m³ or less were detected.

Conclusion

Embodiments of the present disclosure provide a mercury sensor configured to detect mercury in a sample at a concentration of 1 μg/m³ or less. In certain embodiments, the LSPR of the 5 nm particles shifted 1 nm for every 15 adsorbed mercury atoms. The 5 nm particles provided for sensitive measurements because they had a large surface-area-to-volume ratio (e.g., a surface area to volume ratio of 0.2 or more). Assembled into a sub-monolayer film on a 1 cm square quartz chip, the total mass adsorbed per nanometer of LSPR shift was 75 ng. The lowest demonstrated mass limit of detection, using the area probed by the light signal and the mass of mercury required to shift the LSPR wavelength one increment of the wavelength resolution, was 4.6 picograms. In some instances, the concentration limit of detection may depend on the rate of mass transfer. The adsorption process was driven by diffusion and the flux was proportional to mercury vapor concentration. This meant that with the same sampling conditions a sensor chip that took less than 1 minute to detect a 1 μg/m³ sample would take almost 17 hours to detect a 1 ng/m³ sample. In certain embodiments, optimizing the mass flux can facilitate the measuring of ambient levels of mercury (e.g., 1 ng/m³). Changing the sample flow characteristics or coupling the sensor to gold traps are two options that may facilitate measuring 1 ng/m³ or less mercury concentrations. Experimental results, which agreed with mass transfer models, indicated that by increasing the flow rate to 200 LPM a measurement of a 10 ng/m³ can be performed in under 12 hours using embodiments of the mercury sensor disclosed herein.

Example 2

Fiber Optic Substrate

The extent of the evanescent wave into a surrounding medium is given by the penetration depth, $D_p$:

$$D_p = \frac{\lambda}{2\pi n_2 (\sin^2\theta - \sin^2\theta_G)^{0.5}}$$

where λ is the wavelength, $n_1$ is the refractive index of the optical fiber, θ is the angle between the interface and the ray path, and $\theta_G = \arcsin(n_2/n_1)$ with $n_2$ being the refractive index of the surrounding material. For the system investigated here, a silica fiber core surrounded by air, the evanescent wave will extend between 400 and 100 nm from the boundary of the fiber at the resonance peak of the gold nanoparticles (e.g., gold nanorods), which is about 750 nm. Thus, a stripped fiber optic cable provided a substrate for coupling light from the fiber optic cable into the nanoparticles. Additionally, the fiber optic cable provided a convenient platform to expose and measure absorption changes in the nanorods.

Experimental Setup

600 μm inner diameter plastic clad silica fiber optic cables (Thorlabs, Newton, N.J.) were cut to approximately 25 cm, and an approximately 5 cm section of cladding from the middle of the cables was removed by heating with small gas-oxygen torch then rinsing with deionized water and careful rubbing with tissue wipes. The gas-oxygen torch was also used to heat the decladded section of the fiber in order to bend it into a U-shape. The bending was done by hand with a visual guide to maintain consistency.

Figure 7:
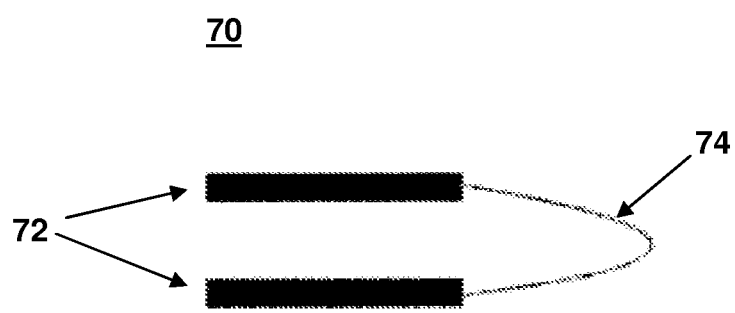
FIG. 7 shows a drawing of an optical fiber mercury sensor, according to embodiments of the present disclosure.

To connect the fiber optic cables to the measurement system SMA 905 connectors were then attached to the ends of the cables. The cables were also attached through the high density polyethylene vial cap. This provided stability that protected the cable from excessive bending or torsion which can easily cause breakage. Additionally, the vial itself provided a platform for further surface treatments of the cable and its exposure to mercury. The connectors and the cable were all secured using Epo-Tek 353ND heat cured epoxy (Precision Fiber Products, Milpitas, Calif.). The final cable assembly is shown in FIG. 7. As shown in FIG. 7, the mercury sensor 70 includes an optical fiber cable with connectors 72 at each end of the cable. Between the connectors is an exposed portion 74 of the cable onto which nanoparticles (not shown) are attached.

After the cables were fabricated, gold nanorods were attached to the bare portion of the fiber optic cable using a method derived from Frederix et al. Briefly, the cables were cleaned in a mild detergent and Millipore purified water (18.2 ohm). They were then further cleaned in 2M NaOH for 1 hour, and a further treatment in a 1:1:5 solution of $H_2O_2$ $NH_3$(aq) and $H_2O$ for 7 min at 80° C. to 90° C. to provide a fresh oxide layer. The cable was then rinsed again in Millipore water and dried before being immersed in a 95:5 methanol, water solution with 2% (v/v) of (3-mercaptopropyl)methyltriethoxysilane. The sample was left overnight, then removed and rinsed in 1 ml of methanol, before being annealed for 10 min at 105° C. Reference spectra were obtained before the nanorods were applied.

400 μl of the gold nanorod solution was applied dropwise from a pipette to the bare portion of the fiber optic cable. This was allowed to dry overnight, and then rinsed with 1 ml of Millipore water. The nanorods were polymer stabilized nanorods (Nsol, Nanopartz, Loveland, Colo.) with a diameter of 25 nm and an axial length of 86 nm. The concentrated nanorods were diluted 1:90 with ethanol. This dilution ratio provided a good balance between aggregation of the nanoparticles and sufficient coverage to provide a strong absorbance response.

Figure 8:
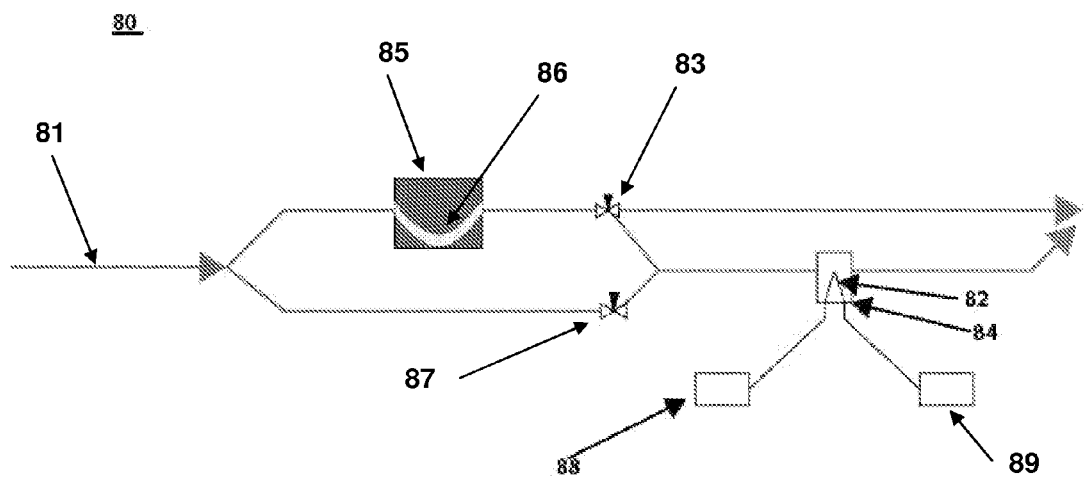
FIG. 8 shows a mercury detection system that includes an optical fiber mercury sensor, according to embodiments of the present disclosure.

Experiments were performed to expose the functionalized fiber optic cable to a known and controlled amount of mercury vapor. The mercury detection system 80 is shown in FIG. 8. The mercury sensor 82 was installed into an enclosed flow cell 84. The system 80 also included a permeation tube 86 (VICI, Houston, Tex.) in a second flow cell 85. The permeation tube 86 contained a saturated two-phase mixture of mercury liquid and vapor inside a membrane permeable to the vapor phase. Light was provided to the mercury sensor 82 by light source 88 and was detected by light detector 89. Air flow 81 flowed through the system 80 (flow direction indicated by arrow). The air flow 81 was directed either through the second flow cell 85 containing the mercury permeation tube 86, or directly to the flow cell 84 containing the mercury sensor 82. The flow of the air flow was controlled by valves 83 and 87.

Purified air from a cylinder was passed through a calibrated flow meter, and then through a temperature controlled section containing the permeation tube. After which the gas mixture flowed through a chamber containing the fiber optic cable before being exhausted. At the exhaust, the mercury concentration was measured with a portable Jerome Mercury Vapor Analyzer, to validate the concentration calculated from the permeation rate and flow rate.

The fiber optic cable was connected to an Ocean Optics HR400 spectrometer attached to a computer running their spectra suite software. The light source was a halogen lamp (DH-2000-BAL, Ocean Optics, Dunedin, Fla.).

Results

The absorbance spectrum of the sensor was compared with the absorbance of the nanorods in solution. With the absorbance calculated from the following equation:

$$a(y) = -\log[(I_s(y) - I_d(y))/(I_0(y) - I_d(y))]$$

where $I_s$ is the intensity count of the sample, $I_d$ is the dark intensity count with the light source covered, and $I_0$ is the intensity of the reference (e.g., the bare fiber optic cable without nanoparticles), all at a specified wavelength (y). The absorbance spectrum of the sensor compared with the absorbance of the nanorods in solution is shown in FIG. 9.

Figure 9:
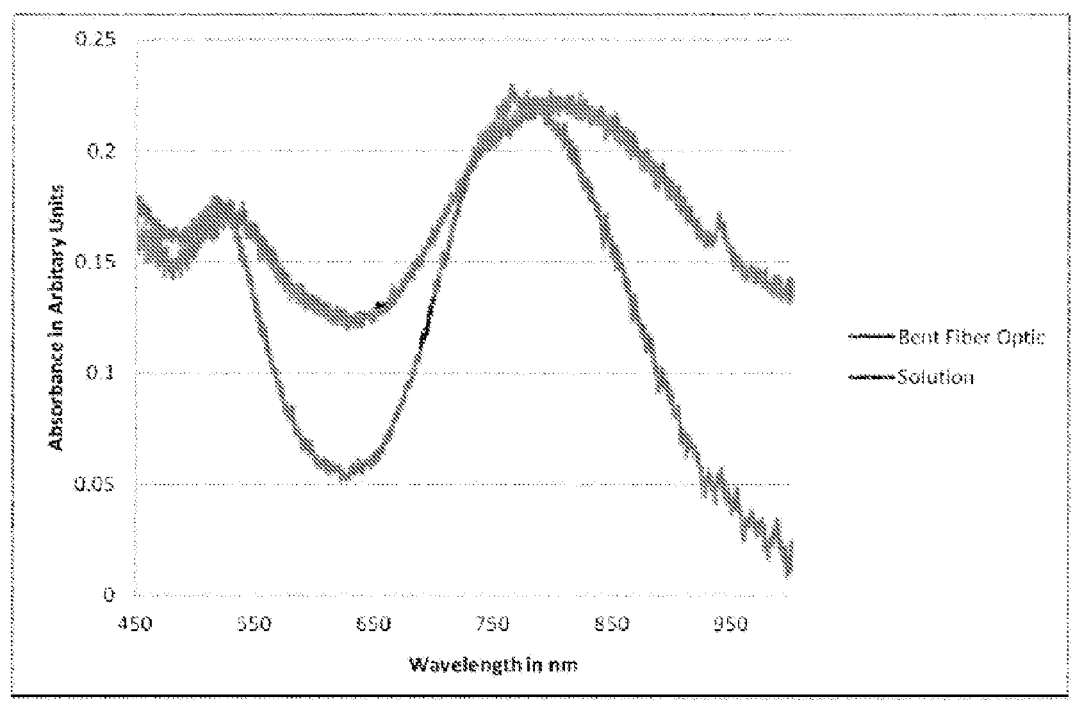
FIG. 9 shows a graph of absorbance vs. wavelength (nm) for a fiber optic mercury sensor compared to elongated nanoparticles in solution, according to embodiments of the present disclosure.

FIG. 9 shows the characteristic double peak of a gold nanorod, but the shape of the absorbance spectra, and the exact location of the longitudinal peak was not the same. This was because the dielectric constant of the material surrounding the nanorods was changing, e.g., from ethanol to silica and air. An increasing dialectic constant should blue shift the longitudinal peak. The slight red shifts and broadening of the peak indicated that the nanorods may be aggregating to some extent.

The final deposition of the nanorods on the fiber optic cable was variable with longitudinal peaks ranging from 718 nm to 834 nm. Additionally, the sensors saturated after a certain amount of time passed, as seen in FIG. 10, which was the typical response of the sensor to an exposure of mercury vapor flow.

Figure 10:
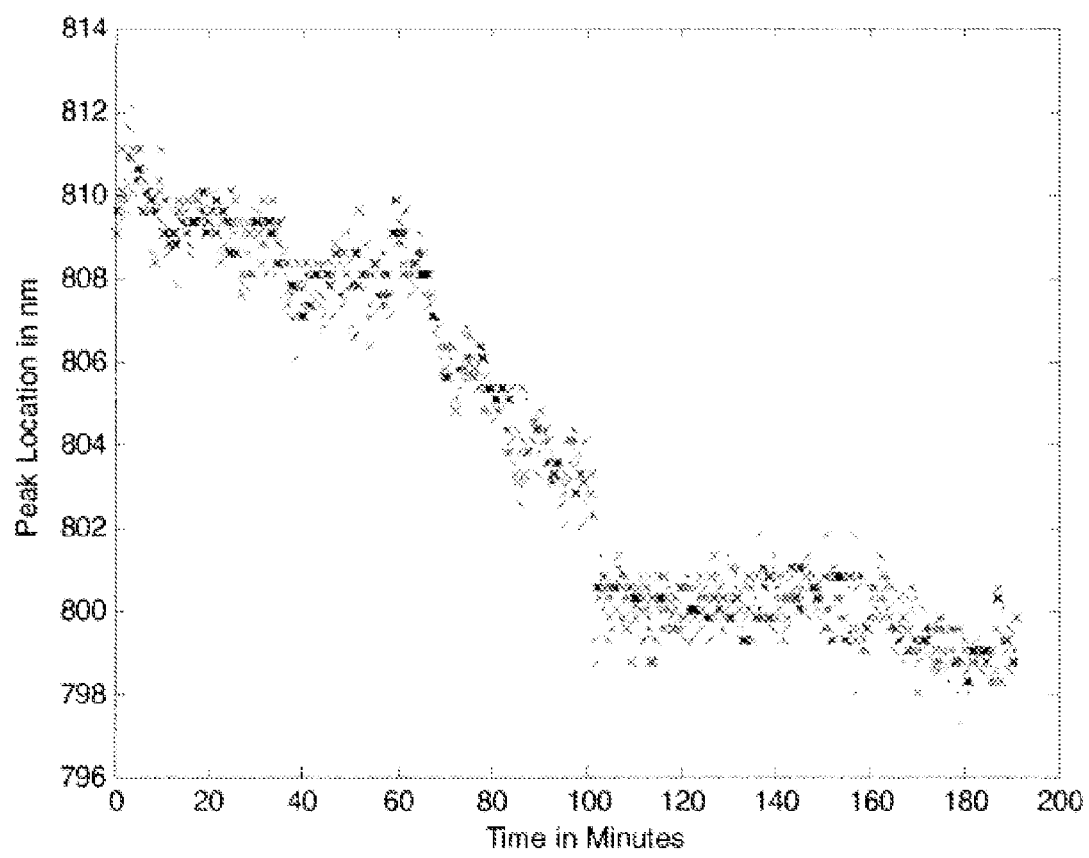
FIG. 10 shows a graph of LSPR peak location (e.g., wavelength) (nm) vs. time (min) for a mercury sensor according to embodiments of the present disclosure.

In FIG. 10, a concentration of 4 μg/m³ was added at minute 69. Peak Location on the y-axis of the graph in FIG. 10 referred to the maximum of the longitudinal LSPR peak as calculated from the absorbance spectrum.

To account for the variability in initial deposition of the nanorods, the saturation of the nanorods, and the noise in the data, the first derivative of the percent change in the peak location with respect to the initial peak was calculated and was found to correlate with the concentration of mercury, as expressed in the following equation:

$$d[Y_p(t)/Y_i]/d_t = f(c)$$

where $Y_p$ is the wavelength of the peak, $Y_i$ is the wavelength of the initial peak, and f(c) is a function of the concentration of mercury.

Figure 11:
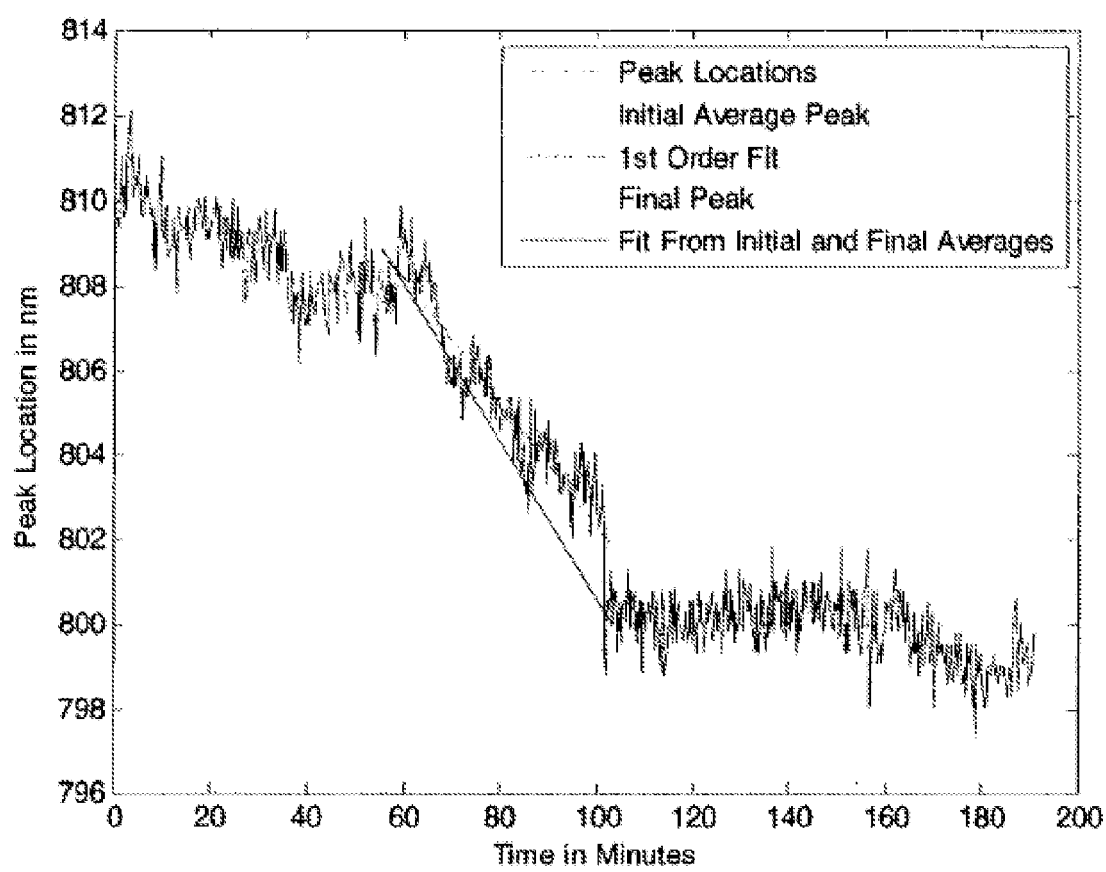
FIG. 11 shows a graph of LSPR peak location (e.g., wavelength) (nm) vs. time (min) with linear regression analysis for a mercury sensor according to embodiments of the present disclosure.

This was calculated by averaging the initial and final peaks, to reduce some of the noise, and then applying a linear regression to the data between the time corresponding to the beginning of the mercury exposure and the time when the final peak was reached. This is represented graphically in FIG. 11.

To calibrate the sensor measurements at relatively high concentration levels, this served the dual purpose of establishing a baseline response for the sensor and validating the calculated concentration, as these concentration levels were within the range of the Jerome 431-X Mercury Vapor Analyzer used. The comparison of the flow rate and the measured concentration is shown in Table 1 below.

TABLE 1

Calibration of Concentration from the Flow Rate with Mercury Vapor Analyzer Data

| Flow Rate (l/min) | Mercury Release (ng/min) | Calculated Concentration (μg/m³) | Measured Concentration (μg/m³) |
|---|---|---|---|
| 0.65 ± 0.1 | 27.7 ± 2.9 | 42.6 ± 2.8 | 26 ± 3 |
| 1.63 ± 0.1 | 27.7 ± 2.9 | 17.0 ± 2.8 | 15 ± 3 |
| 2.44 ± 0.1 | 27.7 ± 2.9 | 11.3 ± 2.8 | 11 ± 3 |
| 3.25 ± 0.1 | 27.7 ± 2.9 | 8.52 ± 2.8 | 9 ± 3 |
| 4.23 ± 0.1 | 27.7 ± 2.9 | 6.55 ± 2.8 | 6 ± 3 |

Figure 12:
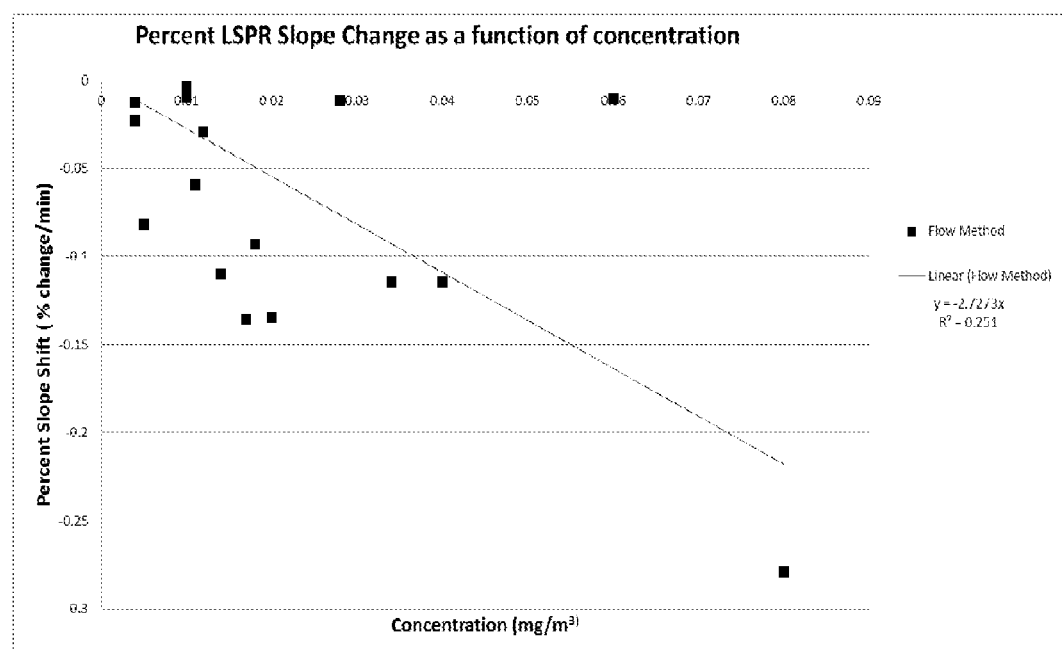
FIG. 12 shows a graph of percent slope per minute (% change/min) vs. concentration (mg/m$^3$) for a mercury sensor according to embodiments of the present disclosure.
Figure 13:
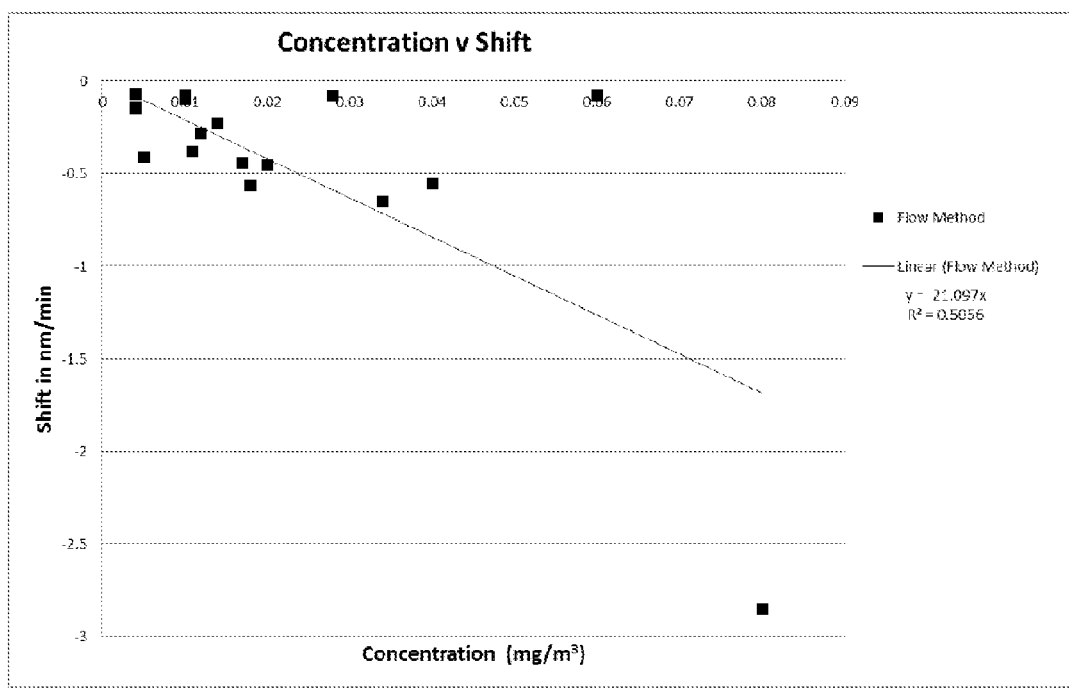
FIG. 13 shows a graph of the shift in peak LSPR wavelength over time (nm/min) vs. mercury concentration (mg/m$^3$), according to embodiments of the present disclosure.

The response of the sensor is shown in FIG. 12, which shows a graph of percent slope per minute (% change/min) vs. concentration (mg/m³). FIG. 13 shows a graph of the slope (e.g., shift in peak LSPR wavelength over time) (nm/min) due to change in concentration (mg/m³).

The response of the percent change in the slope was linearly dependent on the concentration of mercury vapor measured by the sensor (see FIG. 12). The response of the sensor, before saturation, was driven by the diffusion of mercury to the surface. The diffusion coefficient was constant for these conditions, so the transport of mercury to the surface was a linear function of the concentration.

After validation and calibration of the fiber optic sensor, the concentration of mercury was lowered to determine the limit of detection for the system. The limit of detection was determined to be 100 ng/m³ or less. This compares to the typical concentration in the exhaust gas of coal combustion of 1-20 μg/m³.

Example 3

Experimental Setup

Silicon nitride grid (Ted Pella, Redding, Calif.) was incubated in 40 microliters of a 1000:1 dilution of Nanosol rods (Nanopartz, Loveland, Colo.) in ethanol for 20 seconds. The grid was rinsed 4 times in ethanol, dried in air and stored at room temperature in a grid holder. The grid was then imaged in a dark field microscope and in a TEM. Energy dispersive x-ray spectroscopy (EDX) was used to measure the particle composition. After verification in the TEM that a specific bright spot in the dark field image was an isolated gold nanorod (AuNR) the spectra of the AuNR were collected. The background was subtracted and the resulting spectra was divided by the lamp spectrum before analysis of the peak location. The characterization process, TEM, EDX and dark field spectroscopy, was repeated after exposure to Hg.

Mercury exposure took place with a constant concentration and flow rate of mercury vapor in air. The mercury vapor dilution was held in a Teflon sample bag (3 liters). The sample included of a small volume (1-15 ml) of saturated mercury vapor added with a gas-tight syringe to a bag inflated with tank air. A septum lid covered vial with a bead of mercury in air acted as the reservoir for saturated mercury. After injection of mercury vapor into the bag and subsequent mixing, the concentration was verified with a Jerome mercury analyzer. The sample bag was then connected to a Teflon tube containing the AuNR TEM grid. The mercury vapor was drawn through the tube at a constant flow rate of 13 cc/min using a peristaltic pump downstream of the grid.

Results

Figure 14:
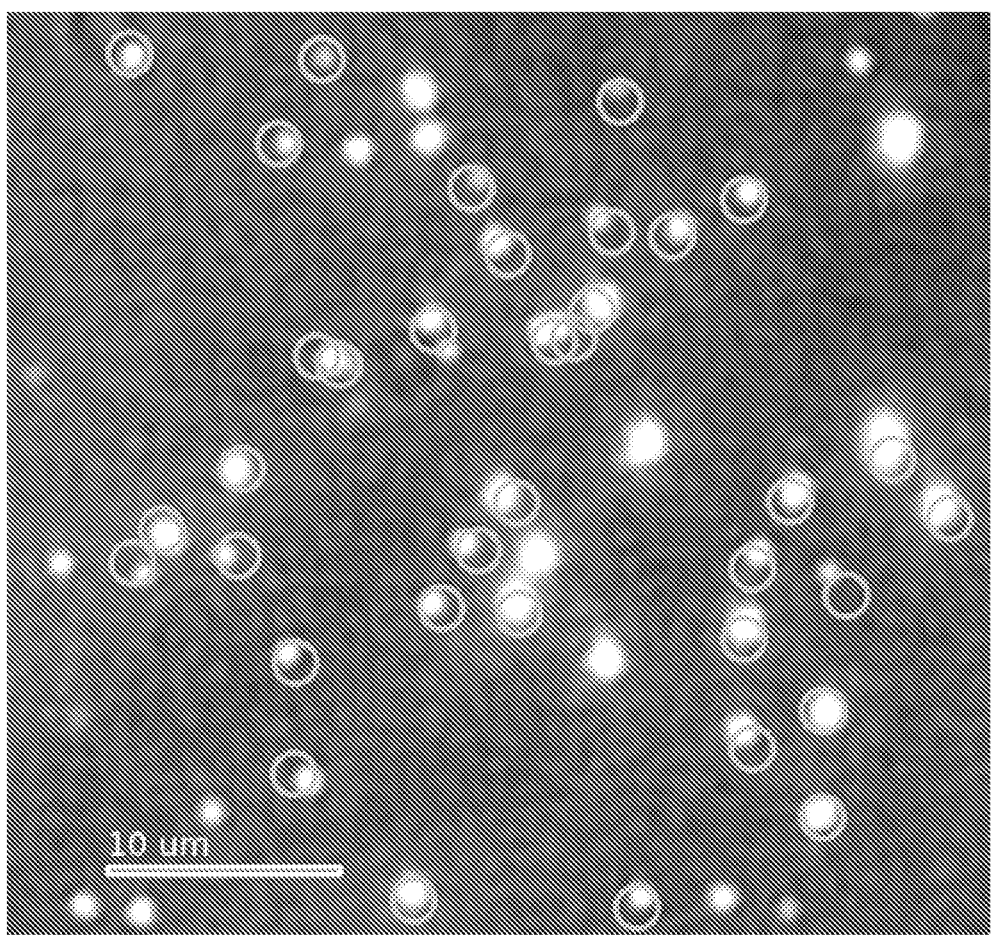
FIG. 14 shows an overlay of a TEM stage map (rings) on a dark field optical image, according to embodiments of the present disclosure.
Figure 15:
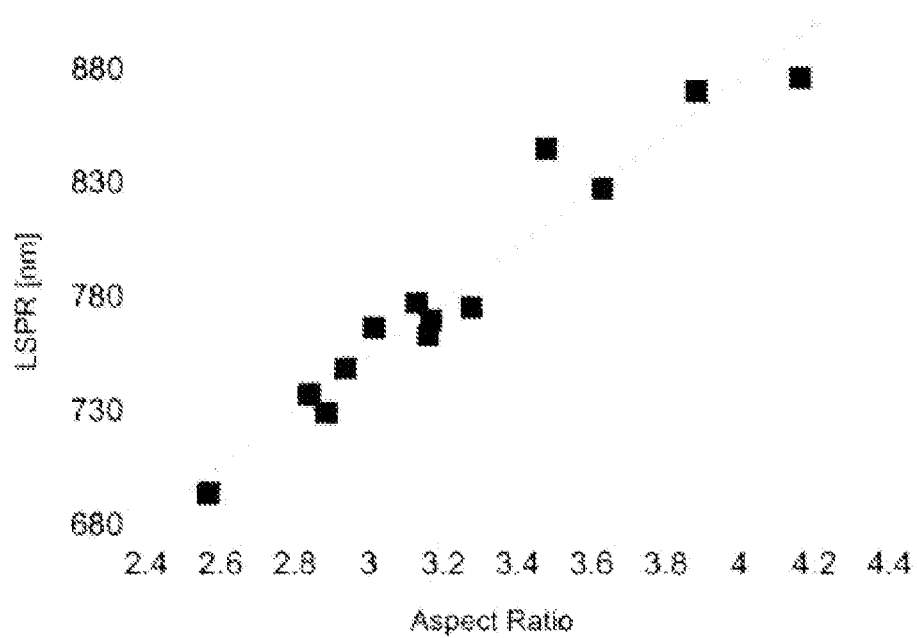
FIG. 15 shows a graph of the peak LSPR wavelength (nm) vs. nanoparticle aspect ratio, according to embodiments of the present disclosure.

Size, shape, and dark field spectrum measurements for specific AuNRs were performed using a combination of optical microscopy at 60× with TEM at 30 kx. The position of each AuNR on the grid window was used as a map to correlate data collected in the two instruments. Each instrument generated a map; the TEM provided the stage position of each image and the AuNR appeared as bright spots in the corresponding dark field image. With the TEM, the grid window was scanned in a 50 μm by 50 μm raster pattern for isolated single AuNRs. A particle was considered isolated if its nearest neighbor was more than 5 μm away. Images of the AuNR, both isolated and bunched, discovered during the raster scan were recorded. Each TEM image taken included the corresponding stage location giving the relative position between images/particles. The recorded positions were plotted with respect to the adjacent grid-window corner and overlaid onto the corresponding dark field image (see FIG. 14), The TEM stage positions were shown as rings in FIG. 14 and the scattered light from the AuNR appeared as the bright spots in the background dark field image. The TEM stage positions coincided with bright spots in the corresponding dark field image, which confirms the accuracy of this method. For further verification, the measured aspect ratio from the TEM images was compared to the longitudinal LSPR wavelength (see FIG. 15). LSPR wavelength increased with aspect ratio.

Figure 16:
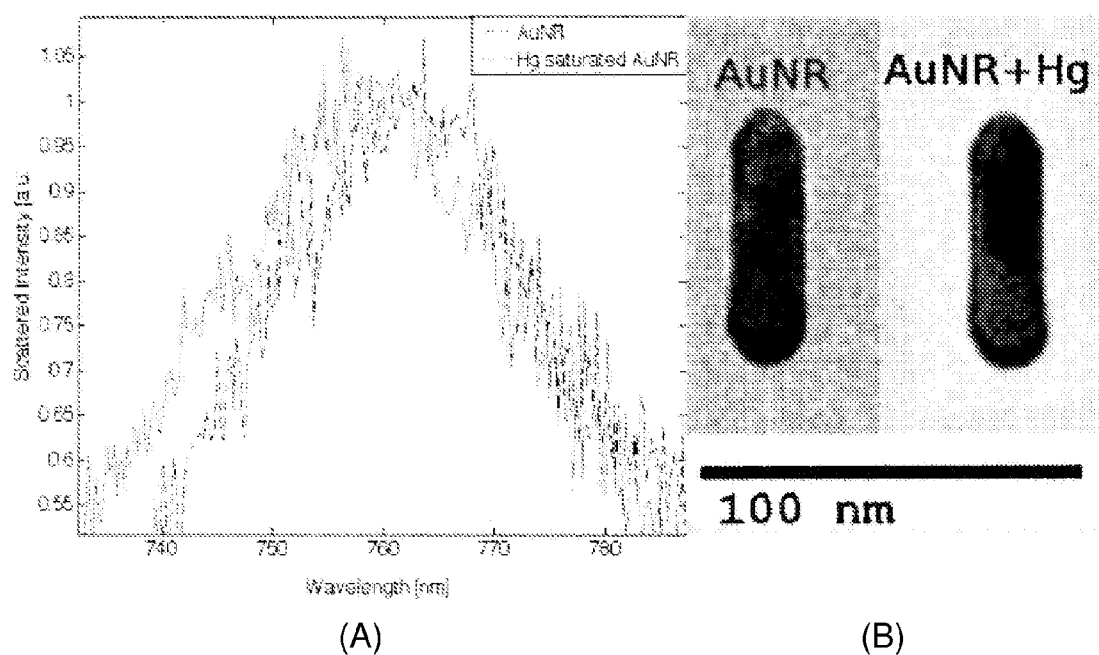
FIG. 16 shows dark field spectra (A) and TEM images (B) for an individual gold nanorod (AuNR) before and after mercury (Hg) saturation, according to embodiments of the present disclosure.

After characterization, the gold particles were exposed to mercury vapor in air for one hour as described above. The amalgam nanorods (e.g., mercury-exposed nanorods) were then reanalyzed with TEM and dark field spectroscopy. TEM images indicated no measurable changes to the shape or size of the nanoparticles. Comparison of the spectra from a single AuNR before and after mercury exposure showed a 2.9 nm blue shift and no changes in geometry (see FIG. 16). EDX analysis showed mercury mass on the sample to be 1.5% the mass of gold. The small change in mass was in agreement with the results of no measureable changes in the particle dimensions as described above.

Figure 17:
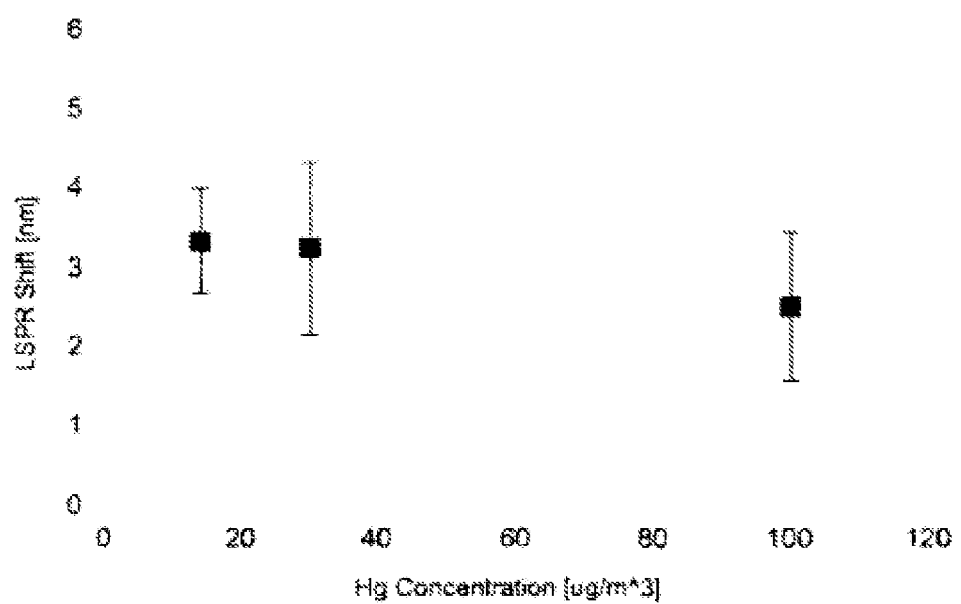
FIG. 17 shows a graph of the shift in the peak LSPR wavelength (nm) vs. mercury (Hg) concentration (μg/m$^3$), according to embodiments of the present disclosure.

Three different mercury concentrations were tested (14, 30 and 98 μg/m$^3$). The LSPR of the amalgam rods blue shifted an average of 3 nm and showed no dependence on vapor concentration of mercury in the tested range (see FIG. 17). The similar response at different mercury concentrations indicated that the particles were saturated and did not collect additional mercury. The shift at saturation determined the dynamic range of the individual AuNR in mercury vapor sensing.

Figure 18:
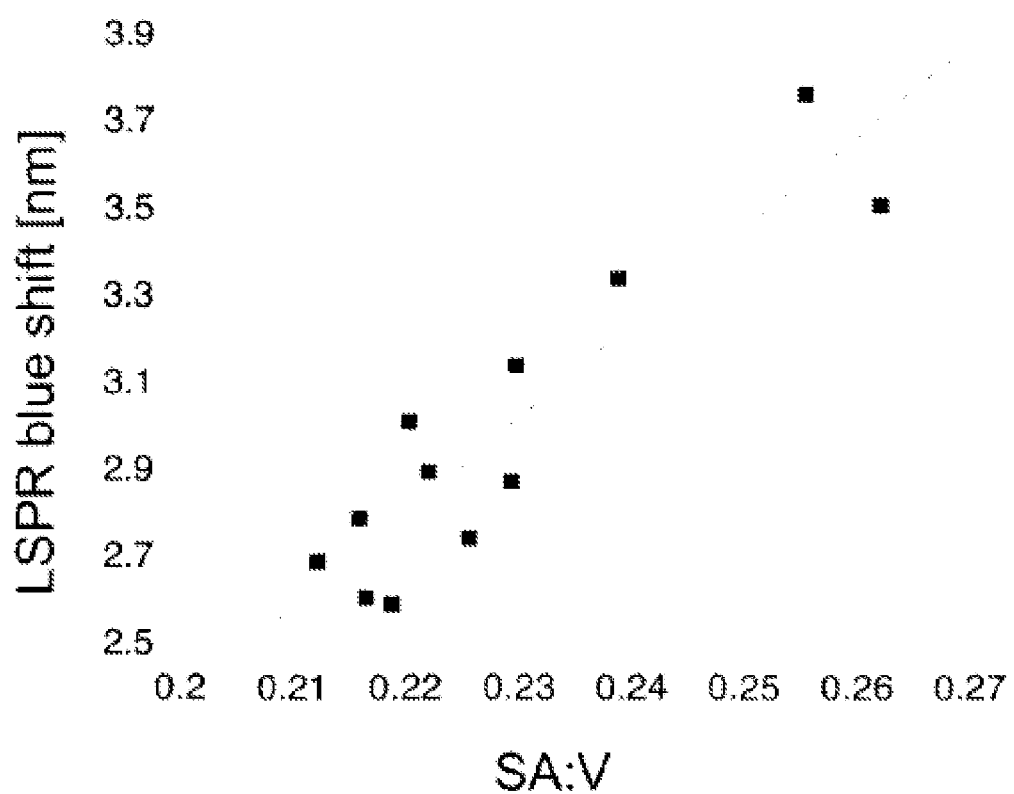
FIG. 18 shows a graph of the shift in the peak LSPR wavelength (nm) vs. nanoparticle surface area to volume (SA:V) ratio, according to embodiments of the present disclosure.

The LSPR blue-shift at saturation depended on individual AuNR dimensions. AuNRs with a larger surface-area-to-volume ratio (SA:V) exhibited a greater dynamic range between their pure-gold and saturated-mercury states (see FIG. 18). The SA:V ratio was calculated using a cylindrical model of each particle using the diameter and length measured from a 30,000× TEM image of the AuNR. The dynamic range showed no correlation with AuNR aspect ratio.

Discussion

Figure 19:
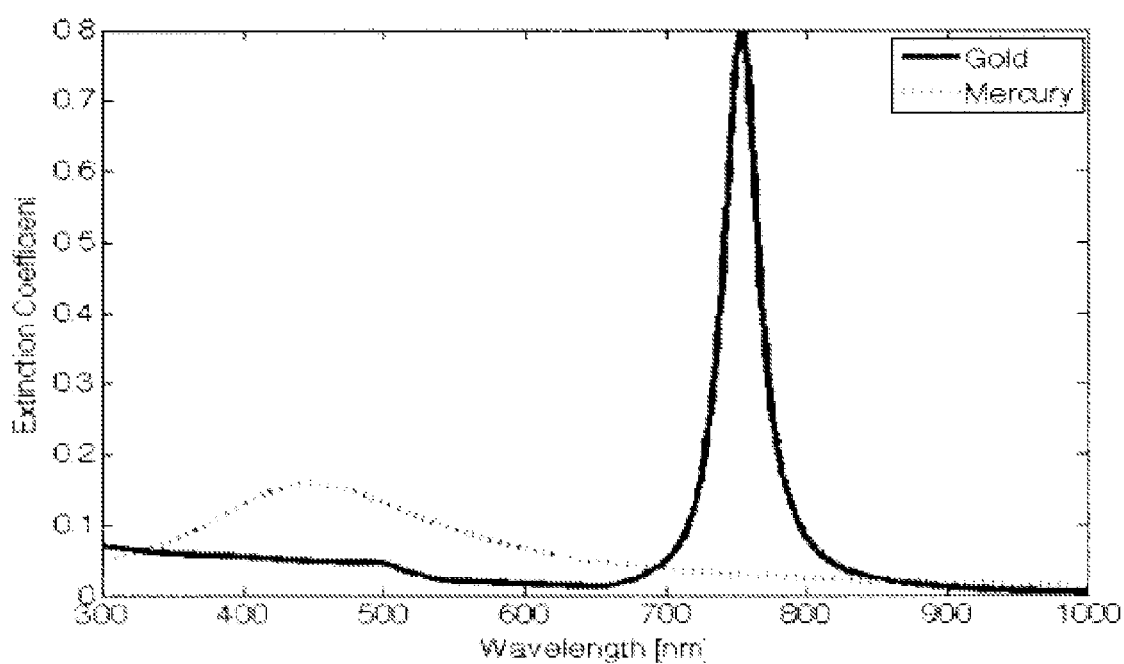
FIG. 19 shows a graph of calculated spectra (extinction coefficient vs. wavelength (nm)) for pure gold (pure-Au) and pure mercury (pure-Hg) nanorods (62 nm long, 20 nm diameter), according to embodiments of the present disclosure.

The wavelength dependence of the extinction coefficient for amalgam nanoparticles was modeled. Bimetallic nanoparticles were found to have LSPR wavelengths with a linear dependence on alloy fraction. This allowed calculation of the adsorbed mass given the initial LSPR peak and the predicted peak for a pure mercury nanorod of the same dimensions and surrounding media. The model, based on Gans theory, provided the absorption spectrum for nanorods of a given size, shape, material and surrounding material. Accordingly, amalgam particle resonance occurred between the pure gold and pure mercury peaks (see FIG. 19) with its relative position linearly proportional to the mass fraction of mercury. The particle dimensions (62 nm long, 20 nm diameter), the metal's known complex dielectric, and the refractive index of the environment were inputted into the model. The model did not provide for the heterogeneity of the particle's immediate surroundings (e.g., a particle with an attached ligand on substrate in air). Instead, an average index of 2 was used, which matched the calculated pure gold peak with the experimentally observed peak. Saturated particles of this size were observed to shift 3 nm, or 1% the difference between the LSPR wavelengths of AuNR and mercury nanorods (HgNR) of those dimensions. This indicated that a saturated AuNR particle consisted of 1% Hg and 99% Au.

The EDX data, size measurements, and LSPR model were in agreement and indicated that the mass of mercury adsorbed by a saturated AuNR was about 1% the nanorod mass. For the nanoparticles used above, a complete monolayer would result in a mass fraction of 2.5% Hg, so the observed 1% Hg indicated 40% monolayer coverage. Nanoparticle surfaces saturate similarly to bulk gold surfaces but the significantly larger SA:V ratio of nanoparticles reduces the gold mass needed to collect a given amount of mercury. For example, the AuNRs tested collected 4.6 times more mercury per gram of gold than a 20 nm thick continuous gold film.

The experiment above showed that the dynamic range of the mercury sensor was linearly dependent on the SA:V ratio, indicating that the mercury was adsorbed with no significant diffusion inwards from the surface. In addition, unlike AuNR based LSPR sensors that monitor the local index of refraction, the performance of the sensors described herein was improved by increasing the SA:V ratio, not the aspect ratio.

Conclusion

The saturation of AuNRs (62×20 nm) with mercury resulted in a 3 nm blue shift of LSPR wavelength, with shifts proportional to SA:V. The average blue shift of 3 nm in LSPR wavelength corresponded to 4 attograms of adsorbed mercury. Saturation occurred in less than an hour of exposure to slow flowing, 13 cc/min, μg/m$^3$ concentrations of mercury vapor. For example, an hour of exposure to 14 μg/m3 mercury produced saturated AuNRs that do not provide further LSPR-shift or mercury collection from additional mercury exposure. The degree of shift before saturation depended on the surface-area-to-volume ratio. Comparison of particle sizes and EDX measurements before and after exposure indicated that particles saturated with a composition of 99% Au and 1% Hg. AuNRs became saturated by adsorbing Hg vapor before the formation of a monolayer of Hg. In Hg sensing and collection, increasing SA:V by controlling shape and size of gold nanoparticle improved performance.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A mercury detection system comprising:
a flow cell comprising a mercury sensor, wherein the mercury sensor comprises:
a transparent substrate; and
a submonolayer of spherical gold nanoparticles on a surface of the substrate, wherein the spherical gold nanoparticles are substantially free of a surface coating;
a light source that directs light from the light source to the mercury sensor;
a light detector that detects a localized surface plasmon resonance (LSPR) signal from the spherical gold nanoparticles; and
a heat source that heats the mercury sensor to regenerate the mercury sensor,
wherein the system determines whether mercury is present in a sample based on a rate of change of the detected LSPR signal from the spherical gold nanoparticles.

2. The mercury detection system of claim 1, wherein the submonolayer has a density of $5 \times 10^{12}$ gold nanoparticles/cm$^2$ or less.

3. The mercury detection system of claim 1, wherein the gold nanoparticles have a surface area to volume ratio of 0.2 or more.

4. The mercury detection system of claim 1, further comprising a gas source in communication with the flow cell and configured to provide a flow of a gas through the flow cell.

5. The mercury detection system of claim 1, wherein the light source comprises a visible light source.

6. The mercury detection system of claim 1, wherein the light detector comprises a UV-Vis photodetector.

7. The mercury detection system of claim 1, wherein the system is configured to detect mercury vapor at a concentration of 100 μg/m$^3$ or less.

8. The mercury detection system of claim 1, wherein the heat source regenerates the mercury sensor without a significant decrease in sensitivity of the mercury sensor.

9. The mercury detection system of claim 1, wherein the sample is a gaseous sample.

10. The mercury detection system of claim 9, wherein the flow cell accommodates a flow rate of the gaseous sample of 0.01 L/min to 20 L/min.

11. A method for determining whether mercury is present in a sample, the method comprising:
contacting a sample to a mercury sensor comprising:
a transparent substrate; and
a submonolayer of spherical gold nanoparticles on a surface of the substrate, wherein the spherical gold nanoparticles are substantially free of a surface coating;
directing light from a light source to the sample-contacted mercury sensor;
detecting a localized surface plasmon resonance (LSPR) signal from the spherical gold nanoparticles;
determining whether mercury is present in the sample based on a rate of change in the detected LSPR signal; and
regenerating the mercury sensor by heating the mercury sensor.

12. The method of claim 11, wherein the contacting comprises flowing a gaseous sample through a flow cell comprising the mercury sensor.

13. The method of claim 12, wherein the gaseous sample has a flow rate of 0.01 L/min to 20 L/min.

14. The method of claim 11, further comprising quantifying the amount of mercury in the sample.

15. The method of claim 14, wherein the quantifying comprises determining the amount of mercury in the sample based on the rate of change in the localized surface plasmon resonance wavelength of the gold nanoparticles.

16. The method of claim 14, wherein the quantifying comprises determining the amount of mercury in the sample based on the rate of change of the absorbance (A) at wavelength ($\lambda$) bands of greatest slope (dA/d$\lambda$) near the localized surface plasmon resonant peak.

17. The method of claim 11, wherein the contacting comprises flowing a gaseous sample through a nozzle perpendicular to the mercury sensor.

18. The method of claim 11, further comprising contacting the sensor with water vapor before contacting the sample to the sensor.

19. The method of claim 11, wherein the regenerating does not significantly decrease sensitivity of the mercury sensor.

20. A system for determining whether mercury is present in a sample, the system comprising:
a nozzle for directing flow of a fluid onto a mercury sensor, wherein the mercury sensor comprises:
a transparent substrate; and
a submonolayer of spherical gold nanoparticles on a surface of the substrate, wherein the spherical gold nanoparticles are substantially free of a surface coating;
a light source that directs light from the light source to the mercury sensor;
a light detector that detects a localized surface plasmon resonance (LSPR) signal from the spherical gold nanoparticles; and
a heat source that heats the mercury sensor to regenerate the mercury sensor,
wherein the system determines whether mercury is present in a sample based on a rate of change of the detected LSPR signal from the spherical gold nanoparticles.

* * * * *

UNITED STATES PATENT AND TRADEMARK OFFICE
CERTIFICATE OF CORRECTION

Page 1 of 1

PATENT NO.        : 9,291,557 B2
APPLICATION NO.   : 14/368499
DATED             : March 22, 2016
INVENTOR(S)       : Jay James It is certified that error appears in the above-identified patent and that said Letters Patent is hereby corrected as shown below:

Specification

In column 1, lines 16-21, "This invention was made with government support under a grant from the National Institute of Environmental Health Sciences, grant number ES04705 and under Contract No. DE-AC02-05CH11231 awarded by the U.S. Department of Energy. The government has certain rights in this invention." should read -- This invention was made with government support under Grant/Contract Number ES004705 awarded by the National Institutes of Health and Grant/Contract Number DE-AC02-05CH11231 awarded by the Department of Energy. The government has certain rights in the invention. --.

Signed and Sealed this
Seventeenth Day of May, 2016

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 9,291,557 B2 |
| APPLICATION NO. | : 14/368499 |
| DATED | : March 22, 2016 |
| INVENTOR(S) | : Jay James |

It is certified that error appears in the above-identified patent and that said Letters Patent is hereby corrected as shown below:

Specification

In column 1, line 34, "CMOS would expand" should read
-- GMOS would expand --.

In column 1, line 38, "A preliminary assessment by CMOS" should read
-- A preliminary assessment by GMOS --.

In column 1, line 50, "confronting the CMOS" should read
-- confronting the GMOS --.

Signed and Sealed this
Nineteenth Day of July, 2016

Michelle K. Lee
*Director of the United States Patent and Trademark Office*